(12) United States Patent
Perry et al.

(10) Patent No.: US 9,993,556 B2
(45) Date of Patent: Jun. 12, 2018

(54) PHARMACEUTICAL COMPOSITIONS COMPRISING FATTY GLYCEROL ESTERS

(71) Applicant: ALKERMES PHARMA IRELAND LIMITED, Dublin (IE)

(72) Inventors: Jason M. Perry, Waltham, MA (US); Magali B. Hickey, Waltham, MA (US); Julius F. Remenar, Waltham, MA (US); Jennifer Vandiver, Waltham, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 265 days.

(21) Appl. No.: 13/801,167

(22) Filed: Mar. 13, 2013

(65) Prior Publication Data
US 2013/0267504 A1  Oct. 10, 2013

Related U.S. Application Data

(60) Provisional application No. 61/612,731, filed on Mar. 19, 2012.

(51) Int. Cl.
| | |
|---|---|
| A61K 47/14 | (2017.01) |
| A61K 47/26 | (2006.01) |
| A61K 31/496 | (2006.01) |
| A61K 31/551 | (2006.01) |
| A61K 9/00 | (2006.01) |
| A61K 47/44 | (2017.01) |

(52) U.S. Cl.
CPC ............ *A61K 47/14* (2013.01); *A61K 9/0019* (2013.01); *A61K 31/496* (2013.01); *A61K 31/551* (2013.01); *A61K 47/26* (2013.01); *A61K 47/44* (2013.01)

(58) Field of Classification Search
CPC .... A61K 31/551; A61K 47/26; A61K 31/496; A61K 47/44; A61K 9/0019
USPC .................. 514/220, 253.07, 253, 254.04
See application file for complete search history.

(56) References Cited

U.S. PATENT DOCUMENTS

| | | |
|---|---|---|
| 2,418,499 A | 4/1947 | Burke |
| 3,266,984 A | 8/1966 | Ueda et al. |
| 3,523,121 A | 8/1970 | Lewis et al. |
| 3,573,308 A | 3/1971 | Ning et al. |
| 3,957,808 A | 5/1976 | Miller et al. |
| 4,160,099 A | 7/1979 | Bodor |
| 4,204,065 A | 5/1980 | Bodor |
| 4,260,769 A | 4/1981 | Stella et al. |
| 4,428,935 A | 1/1984 | Myers |
| 4,443,464 A | 3/1984 | Biedermann et al. |
| 4,594,190 A | 6/1986 | Giani et al. |
| 4,694,006 A | 9/1987 | Bundgaard et al. |
| 4,727,151 A | 2/1988 | Bodor |
| 4,734,416 A | 3/1988 | Banno et al. |
| 4,760,057 A | 7/1988 | Alexander |
| 4,837,337 A | 6/1989 | Murao et al. |
| 4,914,094 A | 4/1990 | Oshiro et al. |
| 4,992,550 A | 2/1991 | Hughes |
| 5,006,528 A | 4/1991 | Oshiro et al. |
| 5,206,386 A | 4/1993 | Narayanan et al. |
| 5,229,382 A | 7/1993 | Chakrabarti et al. |
| 5,236,927 A | 8/1993 | Jones et al. |
| 5,350,747 A | 9/1994 | Howard |
| 5,462,934 A | 10/1995 | Goto et al. |
| 5,532,372 A | 7/1996 | Saji et al. |
| 5,612,346 A | 3/1997 | Mesens et al. |
| 5,700,946 A | 12/1997 | Shimasaki et al. |
| 5,719,303 A | 2/1998 | Yoshida et al. |
| 5,783,589 A | 7/1998 | Latimer et al. |
| 5,945,416 A | 8/1999 | Shannon et al. |
| 5,985,856 A | 11/1999 | Stella et al. |
| 6,127,357 A | 10/2000 | Cliffe et al. |
| 6,133,248 A | 10/2000 | Stella |
| 6,169,084 B1 | 1/2001 | Bunnell et al. |
| 6,180,095 B1 | 1/2001 | Greenwald et al. |
| 6,608,084 B1 | 8/2003 | Bourzat et al. |
| 6,653,312 B1 | 11/2003 | Auvin et al. |
| 6,656,932 B2 | 12/2003 | Picard et al. |
| 6,977,257 B2 | 12/2005 | Parab et al. |
| 7,053,092 B2 | 5/2006 | Jordon et al. |
| 7,112,603 B2 | 9/2006 | Moon et al. |
| 7,115,587 B2 | 10/2006 | Nerurkar et al. |
| 7,160,888 B2 | 1/2007 | Johnson et al. |
| 7,538,121 B2 | 5/2009 | MacDonald et al. |
| 7,550,445 B2 | 6/2009 | Nerurkar et al. |
| 7,807,680 B2 | 10/2010 | Kostanski et al. |

(Continued)

FOREIGN PATENT DOCUMENTS

| | | |
|---|---|---|
| DE | 1273533 B | 7/1968 |
| EP | 0 925 061 B1 | 12/2005 |

(Continued)

OTHER PUBLICATIONS

Shintani et al: A new method to determine the irritation of drugs after intramuscular injection in rabbits; Toxicology and Applied Pharmacology; Academic Press, U.S., Sep. 1, 1967; vol. 11, No. 2, pp. 293-295.
International Search Report, PCT/US2012/029625, dated Aug. 28, 2012, 8 pages.
International Preliminary Report on Patentability, PCT/US2012/029625, dated Sep. 24, 2013, 11 pages.
International Search Report, PCT/US2013/030933, dated Jun. 26, 2013, 5 pages.
Written Opinion corresponding to International Patent Application No. PCT/US2013/030933, dated Jun. 26, 2013, 9 pages.
International Search Report with Written Opinion corresponding to International Patent Application No. PCT/US2013/030916, dated Aug. 27, 2013, 18 pages.
International Search Report with Written Opinion corresponding to International Patent Application No. PCT/US2013/030945, dated Jun. 27, 2013, 17 pages.
International Search Report and Written Opinion for International Application No. PCT/US2015/021448, dated Jun. 19, 2015, 12 pages.

(Continued)

*Primary Examiner* — Jennifer M Kim
(74) *Attorney, Agent, or Firm* — Lathrop Gage LLP; Brian C. Trinque

(57) ABSTRACT

The present invention relates to a pharmaceutical composition comprising glycerol esters of a fatty acid, wherein the compositions are useful for the delivery of anti-psychotic drugs.

13 Claims, 1 Drawing Sheet

(56) References Cited

U.S. PATENT DOCUMENTS

| | | | |
|---|---|---|---|
| 7,910,577 B2 | 3/2011 | Liversidge et al. | |
| 7,981,906 B2 * | 7/2011 | Dull et al. | 514/305 |
| 8,017,615 B2 | 9/2011 | Bando et al. | |
| 8,030,313 B2 | 10/2011 | Kostanski et al. | |
| 8,338,427 B2 | 12/2012 | Brown | |
| 8,338,428 B2 | 12/2012 | Brown | |
| 8,399,469 B2 | 3/2013 | Bando et al. | |
| 8,431,576 B2 | 4/2013 | Remenar et al. | |
| 8,518,421 B2 | 8/2013 | Kothari et al. | |
| 8,536,328 B2 | 9/2013 | Remenar et al. | |
| 8,580,796 B2 | 11/2013 | Bando et al. | |
| 8,642,600 B2 | 2/2014 | Jordan et al. | |
| 8,642,760 B2 | 2/2014 | Bando et al. | |
| 9,034,867 B2 | 5/2015 | Perry et al. | |
| 9,193,685 B2 | 11/2015 | Perry et al. | |
| 9,351,976 B2 | 5/2016 | Perry et al. | |
| 9,452,131 B2 | 9/2016 | Hickey et al. | |
| 9,526,726 B2 | 12/2016 | Hickey et al. | |
| 2002/0146455 A1 | 10/2002 | Kundu et al. | |
| 2002/0176841 A1 | 11/2002 | Barker et al. | |
| 2003/0064998 A1 | 4/2003 | Francois et al. | |
| 2003/0077297 A1 | 4/2003 | Chen et al. | |
| 2004/0101557 A1 | 5/2004 | Gibson et al. | |
| 2005/0019436 A1 | 1/2005 | Burch et al. | |
| 2005/0032811 A1 | 2/2005 | Brown et al. | |
| 2005/0079185 A1 | 4/2005 | Parisot et al. | |
| 2005/0203089 A1 | 9/2005 | Starrett, Jr. et al. | |
| 2005/0282821 A1 | 12/2005 | Lesur et al. | |
| 2006/0040922 A1 | 2/2006 | Greco et al. | |
| 2006/0142333 A1 | 6/2006 | MacDonald et al. | |
| 2006/0154918 A1 | 7/2006 | Liversidge et al. | |
| 2006/0194345 A1 * | 8/2006 | Uchiyama et al. | 436/518 |
| 2006/0293217 A1 | 12/2006 | Barker et al. | |
| 2007/0031513 A1 | 2/2007 | Kikuchi et al. | |
| 2007/0148100 A1 | 6/2007 | Jenkins | |
| 2007/0191611 A1 | 8/2007 | Rao et al. | |
| 2008/0085888 A1 | 4/2008 | Breining et al. | |
| 2008/0186971 A1 | 8/2008 | Carmichael et al. | |
| 2008/0233053 A1 | 9/2008 | Gross et al. | |
| 2008/0261954 A1 | 10/2008 | Maelicke | |
| 2008/0312199 A1 | 12/2008 | Glinsky | |
| 2008/0318905 A1 | 12/2008 | Muhammad et al. | |
| 2009/0053329 A1 | 2/2009 | Peters et al. | |
| 2009/0068290 A1 | 3/2009 | Bourin et al. | |
| 2009/0118242 A1 | 5/2009 | Burch et al. | |
| 2009/0143403 A1 | 6/2009 | Brown | |
| 2009/0163519 A1 | 6/2009 | Vermeulen et al. | |
| 2009/0163545 A1 | 6/2009 | Goldfarb | |
| 2009/0169632 A1 | 7/2009 | Lu et al. | |
| 2009/0311347 A1 | 12/2009 | Oronsky et al. | |
| 2010/0197641 A1 | 8/2010 | Mazess et al. | |
| 2010/0203129 A1 | 8/2010 | Andersen et al. | |
| 2010/0286136 A1 | 11/2010 | Jones et al. | |
| 2010/0292316 A1 | 11/2010 | Sanders et al. | |
| 2010/0331356 A1 | 12/2010 | Legen et al. | |
| 2011/0003828 A1 | 1/2011 | Blumberg et al. | |
| 2011/0015156 A1 | 1/2011 | Remenar et al. | |
| 2011/0105536 A1 | 5/2011 | Lewyn-Briscoe et al. | |
| 2011/0166128 A1 | 7/2011 | Remenar et al. | |
| 2011/0166156 A1 | 7/2011 | Blumberg et al. | |
| 2011/0166194 A1 | 7/2011 | Blumberg et al. | |
| 2011/0178068 A1 | 7/2011 | Almarsson et al. | |
| 2011/0195095 A1 | 8/2011 | Liversidge et al. | |
| 2011/0236478 A1 | 9/2011 | Dokou et al. | |
| 2011/0275803 A1 | 11/2011 | Remenar et al. | |
| 2011/0319422 A1 | 12/2011 | Blumberg et al. | |
| 2012/0015866 A1 | 1/2012 | Blumberg et al. | |
| 2012/0238552 A1 | 9/2012 | Perry et al. | |
| 2013/0003046 A1 | 1/2013 | Izawa et al. | |
| 2013/0096089 A1 | 4/2013 | Remenar et al. | |
| 2013/0267503 A1 | 10/2013 | Perry et al. | |
| 2013/0267505 A1 | 10/2013 | Perry et al. | |
| 2014/0088115 A1 | 3/2014 | Perry et al. | |
| 2015/0258115 A1 | 9/2015 | Perry et al. | |
| 2015/0265529 A1 | 9/2015 | Hickey et al. | |
| 2016/0038508 A1 | 2/2016 | Perry et al. | |
| 2016/0136279 A1 | 5/2016 | Perry et al. | |
| 2016/0263111 A1 | 9/2016 | Hickey et al. | |

FOREIGN PATENT DOCUMENTS

| | | |
|---|---|---|
| EP | 1 891 956 A1 | 12/2008 |
| GB | 0 849 541 A1 | 9/1960 |
| GB | 2 017 701 A | 10/1979 |
| GB | 2054371 A | 2/1981 |
| JP | S60-002331 A | 1/1985 |
| WO | 1990/014080 A1 | 11/1990 |
| WO | 1991/000863 A1 | 1/1992 |
| WO | 1993/025197 A1 | 12/1993 |
| WO | 1996/012725 A1 | 5/1996 |
| WO | 1997/043284 A1 | 11/1997 |
| WO | 1999/033846 A2 | 7/1999 |
| WO | 2002/049573 A2 | 6/2002 |
| WO | 2002/096351 A2 | 12/2002 |
| WO | 2004/012671 A2 | 2/2004 |
| WO | 2004/026864 A1 | 4/2004 |
| WO | 2004/067546 A1 | 8/2004 |
| WO | 2004/089925 A1 | 10/2004 |
| WO | 2005/016262 A2 | 2/2005 |
| WO | 2005/066165 A1 | 7/2005 |
| WO | 2005/079807 A1 | 9/2005 |
| WO | 2006/037090 A2 | 4/2006 |
| WO | 2006/055603 A2 | 5/2006 |
| WO | 2006/090273 A2 | 8/2006 |
| WO | 2007/018943 A2 | 2/2007 |
| WO | 2007/059111 A2 | 5/2007 |
| WO | 2008/124030 A1 | 10/2008 |
| WO | 2009/052467 A1 | 4/2009 |
| WO | WO2009/060473 A2 | 5/2009 |
| WO | 2010/135703 A2 | 11/2010 |
| WO | 2010/151689 A1 | 12/2010 |
| WO | WO 2010/151711 A1 | 12/2010 |
| WO | 2011/084846 A1 | 7/2011 |
| WO | 2011/084848 A2 | 7/2011 |
| WO | WO2012/129156 A1 | 9/2012 |
| WO | 2013/142198 A1 | 9/2013 |
| WO | 2013/142202 A1 | 9/2013 |
| WO | 2013/142205 A1 | 9/2013 |
| WO | 2014/080285 A2 | 5/2014 |
| WO | 2015/143145 A1 | 9/2015 |

OTHER PUBLICATIONS

International Search Report and Written Opinion for International Application No. PCT/US2013/060677, dated Feb. 20, 2014, 6 pages.

International Search Report and Written Opinion for International Application No. PCT/IB2013/002995, dated Jun. 18, 2014, 11 pages.

U.S. Appl. No. 14/714,621, filed May 18, 2015, Jason M. Perry et al.

U.S. Appl. No. 14/688,050, filed Apr. 16, 2015, Jason M. Perry et al.

U.S. Appl. No. 14/663,042, filed Mar. 19, 2015, Magali B. Hickey et al.

Partial File History of U.S. Appl. No. 13/423,606, filed Mar. 19, 2012, 62 pages.

Park et al. (1999) "Preparation and evaluation of flurbiprofen-loaded microemulsion for parenteral delivery," International Journal of Pharmaceutics. 181(2)173-179.

Strickley et al. (2004) "Solubilizing Excipients in Oral and Injectable Formulations," Pharmaceutical Research. 21(2):201-230.

U.S. Appl. No. 13/423,606, filed Mar. 19, 2012, 2012/0238552, Sep. 20, 2012, U.S. Pat. No. 9,034,867, May 19, 2015, Jason M. Perry.

U.S. Appl. No. 14/688,050, filed Apr. 16, 2015, 2016/0038508, Feb. 11, 2016, Jason M. Perry.

U.S. Appl. No. 14/714,621, filed May 18, 2015, 2015/0258115, Sep. 17, 2015, U.S. Pat. No. 9,351,976, May 31, 2016, Jason M. Perry.

U.S. Appl. No. 15/154,562, filed May 13, 2016, Jason M. Perry.

U.S. Appl. No. 15/388,554, filed Dec. 22, 2016, Jason M. Perry.

U.S. Appl. No. 13/801,025, filed Mar. 13, 2013, 2013/0267503, Oct. 10, 2013, Jason M. Perry.

(56) References Cited

OTHER PUBLICATIONS

U.S. Appl. No. 13/801,167, filed Mar. 13, 2013, 2013/0267504, Oct. 10, 2013, Jason M. Perry.
U.S. Appl. No. 13/801,344, filed Mar. 13, 2013, 2013/0267505, Oct. 10, 2013, Jason M. Perry.
U.S. Appl. No. 14/031,842, filed Sep. 19, 2013, 2014/0088115, Mar. 27, 2014, U.S. Pat. No. 9,193,685, Nov. 24, 2015, Jason M. Perry.
U.S. Appl. No. 14/882,069, filed Oct. 13, 2015, 2016/0136279, May 19, 2016, Jason M. Perry.
U.S. Appl. No. 14/663,042, filed Mar. 19, 2015, 2015/0265529, Sep. 24, 2015, U.S. Pat. No. 9,452,131, Sep. 27, 2016, Magali B. Hickey.
U.S. Appl. No. 15/164,473, filed May 25, 2016, 2016/0263111, Sep. 15, 2016, U.S. Pat. No. 9,526,726, Dec. 27, 2016, Magali B. Hickey.
Akers et al. (1987) "Formulation Design and Development of Parenteral Suspensions," Journal Parenteral Science and Technology. 41(3):88-96.
Belikov (1993) "ХИМИЯ: Общая Фармацевтическая ХИМИЯ [General Chemistry: Pharmaceutical Chemistry]," Part 1. Moscow, Russia. pp. 43-45.—with English machine translation.
Blakenship et al. (2010) "Aripiprazole for irritability associated with autistic disorder in children and adolescents aged 6-17 years," Ped. Health. 4(4):375-381.
Chang et al. (1996) "Development of a stable freeze-dried formulation of recombinant human interleukin-1 receptor antagonist," Pharm. Res. 13:243-249.
Chueshov (2002) "[Industrial technology of medicaments]," vol. 1. p. 24—with English machine translation.
Cocoman et al. (2008) "Intramuscular injections: a review of best practice for mental health nurses," Journal of Psychiatric and Mental Health Nursing. 15:424-434.
Dai et al. (2007) "Parallel screening approach to identify solubility-enhancing formulations for improved bioavailability of a poorly water-soluble compound using milligram quantities of material," International Journal of Pharmaceutics. 336:1-11.
Lieberman et al.: Eds. (1997) Pharmaceutical Dosage Forms: Disperse Systems. vol. 2. pp. 18-22, 285-301.
Mackenzie (1977) "Non-Equilibrium Freezing Behaviour of Aqueous Systems [and Discussion]," Philosophical Transactions of the Royal Society of London. 278(959):167-189.
Pearson Education, Inc. (1995) "Medication Adminstration Techniques: Injections," [Last Accessed Oct. 30, 2015].
Porras et al. (2004) "Studies of formation of W/O nano-emulsions," Colloids and Surfaces A: Physicochem. Eng. Aspects. 249:115-118.
Shinde et al. (2011) "Microemulsions and Nanoemulsions for Targeted Drug Delivery to the Brain," Current Nanoscience. 7:119-133.
Tang et al. (2004) "Design of freeze-drying processes for pharmaceuticals: practical advice," Pharm. Res. 21:191-200.
Workman (1999) "Safe injection techniques," Nursing Standard. 13(39):47-53.
World Health Organization (2003) "Annex 9: Guide to good storage practices for pharmaceuticals," WHO Technical Report Series, No. 908.
Lieberman et al.: Eds. (1997) Pharmaceutical Dosage Forms: Disperse Systems. vol. 2. p. 18.
U.S. Appl. No. 15/349,243, filed Nov. 11, 2016, Magali B. Hickey.

\* cited by examiner

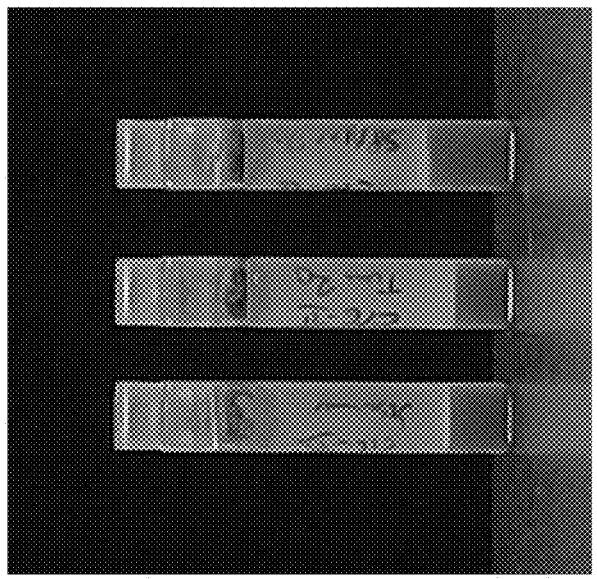

| Sample | All samples contain 10% Compound O-7 in 0.2% aqueous polysorbate 20 | | |
|---|---|---|---|
| | Left | Center | Right |
| Additional component | 0.5 % sesame oil | none | 0.5% Sorbitan laurate |
| Sediment height 4 days after homogenization* | 12.5 mm | 11 mm | 18 mm |
| % increase in sediment height relative to polysorbate 20 alone | 14 % | reference | 64 % |

* Sediment height measured using a ruler with the above picture, not measuring directly on the vial.

PHARMACEUTICAL COMPOSITIONS COMPRISING FATTY GLYCEROL ESTERS

RELATED APPLICATIONS

This application claims priority from U.S. Provisional Patent Application 61/612,731, filed on Mar. 19, 2012, the contents of which are incorporated by reference in their entirety.

TECHNICAL FIELD

The present invention relates to an injectable, pharmaceutical composition comprising a glycerol ester of a fatty acid, wherein the fatty acid comprises 4 to 28 carbon atoms. These compositions are useful for the delivery of antipsychotic drugs.

BACKGROUND OF THE INVENTION

U.S. Pat. Nos. 4,734,416 and 5,006,528 discloses aripiprazole, 7-{4-[4-(2,3-dichlorophenyl)-1-piperazinyl]butoxy}-3,4-dihydro-2(1H)-quinolinone or 7-{4-[4-(2,3-dichlorophenyl)-1-piperazinyl]butoxy}-3,4-dihydro carbostyril, as an atypical antipsychotic agent useful in the treatment of schizophrenia, bipolar disease, depression and other CNS disorders. Aripiprazole has the following chemical structure:

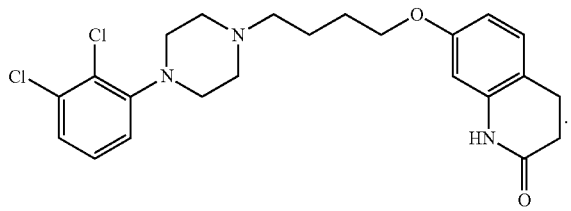 [SMILES: O=C1CCc2ccc(OCCCCN3CCN(c4cccc(Cl)c4Cl)CC3)cc2N1]

Aripiprazole is sold under the tradename Abilify®. It acts as a dopamine $D_2$ partial agonist, serotonin $5\text{-HT}_{1A}$ receptor agonist and is an antagonist of the serotonin $5\text{-HT}_{2A}$ receptor. Abilify® is currently administered orally on a once-a-day dosing schedule as Abilify® (aripiprazole) Tablets, Abilify Discmelt® (aripiprazole) Orally Disintegrating Tablets and Abilify® (aripiprazole) Oral Solution. In one embodiment, Abilify® Injection for intramuscular use is a rapid-acting solution product for treating agitation associated with schizophrenia and bipolar disease. Poor and variable patient compliance with a once-a-day dosing schedule of psychiatric drugs has been reported.

Efforts have been made to provide drug dosage forms that may increase the compliance of patients and thereby lower the rate of relapse in the treatment of schizophrenia. U.S. Pat. No. 7,807,680 and U.S. Publication No. 2005/0032811 describe long-acting aripiprazole sterile injectable formulations. Studies on aripiprazole free base injections showed a prolonged pharmacokinetic profile, but incidents of unacceptable (moderate to severe) tissue irritation following IM and SC injection were also reported.

U.S. Pat. No. 7,115,587 discloses an injectable formulation that delivers an aripiprazole solution complexed with a substituted β-cyclodextrin to the muscular site with diminished irritation as compared to injectable suspensions containing uncomplexed aripiprazole. The Abilify® injection for intramuscular use is a single-dose, ready to use vial consisting of 9.75 mg/1.3 ml of aripiprazole and 150 mg/ml of sulfobutylether β-cyclodextrin. Formulation challenges due to drug loading and poor solubility of aripiprazole in β-cyclodextrin at neutral pH have been reported.

Olanzapine (1,2-methyl-4-(4-methyl-1-piperazinyl)-10H-thieno[2,3-b][1,5]benzodiazepine) is a second generation antipsychotic drug marketed as Zyprexa®. It is useful for the treatment of disorders such as schizophrenia, bipolar disorder, psychotic depression and Tourette syndrome. This active pharmaceutical ingredient acts as an antagonist on $5\text{-HT}_2$ serotonin receptors as well as the $D_1/D_2$ dopamine receptors, while also exhibiting anticholinergic and antimuscarinic properties. Olanzapine belongs to the benzodiazepine family, and has the following structure:

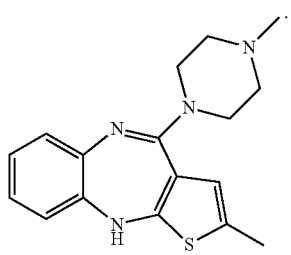 [SMILES: Cc1cc2c(s1)Nc1ccccc1N=C2N1CCN(C)CC1 ; "."]

This compound is disclosed, for example, in U.S. Pat. Nos. 5,229,382 and 6,169,084. An extended release intramuscular injection product containing the water-insoluble salt olanzapine pamoate monohydrate is approved for use in schizophrenia. Like aripiprazole, olanzapine can cause adverse site reactions when injected into a subject.

SUMMARY OF THE INVENTION

There exists a need for improved pharmaceutical compositions of aripiprazole, olanzapine, prodrugs thereof, and other anti-psychotic agents, for extended release use, thereby improving patient compliance and optimizing the pharmacological profile of the active agent.

Provided herein are pharmaceutical compositions comprising (a) a water-insoluble antipsychotic agent; (b) a glycerol ester of a fatty acid, wherein the fatty acid comprises 4 to 28 carbon atoms, and the glycerol ester is a mono, di, or triglyceride; and (c) an aqueous vehicle; wherein the composition forms an aqueous, flocculated, injectable suspension. The composition can comprise additional components, such as (d) a polyoxyethylene derivative of a sorbitan ester of a carboxylic acid, wherein the carboxylic acid comprises 8-20 carbon atoms (e.g., polysorbate 20). The pharmaceutical composition can be injectable.

These pharmaceutical compositions can take a variety of forms. Such forms include, but are not limited to, completely dispersed and flocculated systems.

As described below, the pharmaceutical compositions described herein have a number of advantages. For example, the compositions can be easily resuspended by the user, e.g., through shaking by hand, in a short time prior to administration. In another example, the pharmaceutical compositions, e.g., flocculated systems, can be used to improve the local tissue reaction of antipsychotic drugs in extended release formulations. By mitigating the adverse results associated with the injection of these drugs, drug compliance will be greatly improved.

In an embodiment, of the pharmaceutical composition, the fatty acid comprises 6 to 20 carbon atoms. The glycerol ester can be esters of oleic acid, linoleic acid, linolenic acid, stearic acid, palmitic acid, capric acid, lauric acid or caprylic acid. The glycerol ester can be mixtures of any or all of these specific esters.

The pharmaceutical compositions can comprise one or more components that are comprised of a glycerol ester. Examples of such components include, but are not limited to, sesame oil, olive oil, soybean oil, coconut oil, Imwitor 308, Imwitor 742, Imwitor 312, or Imwitor 928.

In an embodiment, the pharmaceutical composition has a water-insoluble antipsychotic agent that is a aripiprazole, a compound of formula I, or a compound of formula II, or pharmaceutically acceptable salts, hydrates, or solvates thereof:

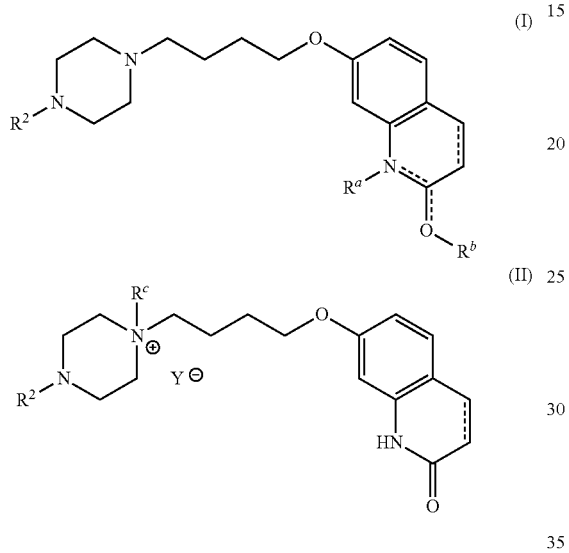

wherein
$R^a$ is absent, and $R^b$ is —CH$_2$OC(O)R$^1$, —CH$_2$OC(O)OR$^1$, —CH$_2$OC(O)N(R$^1$)$_2$ or —C(O)R$^1$;
or
$R^b$ is absent, and $R^a$ is —CH$_2$OC(O)R$^1$, —CH$_2$OC(O)OR$^1$, —CH$_2$OC(O)N(R$^1$)$_2$ or —C(O)R$^1$;
$R^c$ is —CH$_2$OC(O)R$^1$, —CH$_2$OC(O)OR$^1$, —CH$_2$OC(O)N(R$^1$)$_2$ or —C(O)R$^1$;
wherein each $R^1$ is independently selected from the group consisting of hydrogen, substituted or unsubstituted aliphatic, and substituted or unsubstituted aryl; and
wherein each $R^2$ is selected from the group consisting of substituted or unsubstituted aryl and substituted or unsubstituted heteroaryl;
wherein $Y^\ominus$ is a pharmaceutically acceptable counterion; and
wherein ═══ represents a single or double bond.

In another embodiment, the pharmaceutical composition has a water-insoluble antipsychotic agent that is Compound A-4 or Compound A-7:

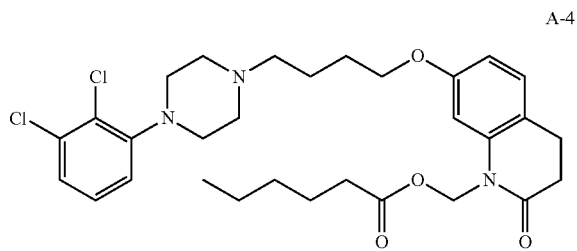

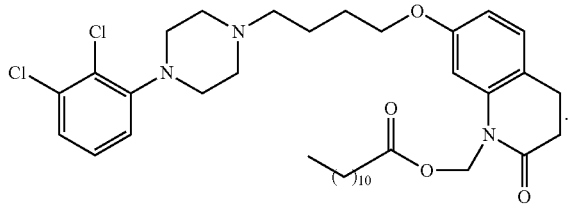

In another embodiment, the pharmaceutical composition has a water-insoluble antipsychotic agent that is olanzapine, a compound of formula III, a compound of formula IV, or a compound of formula V, or pharmaceutically acceptable salts, hydrates, or solvates thereof:

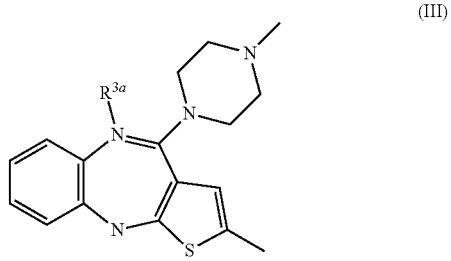

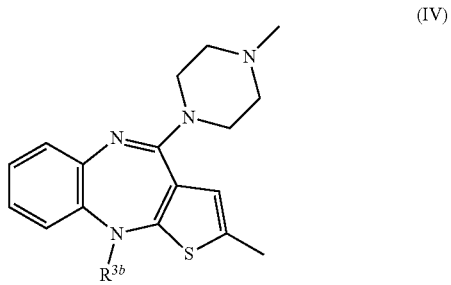

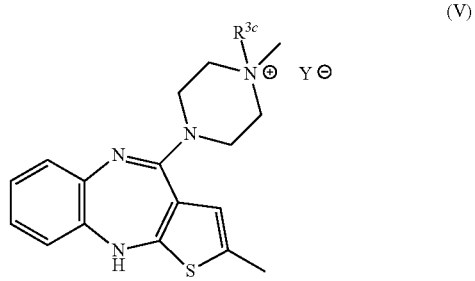

wherein $R^{3a}$, $R^{3b}$, and $R^{3c}$ are independently —CH$_2$OC(O)R$^1$, —CH$_2$OC(O)OR$^1$, —CH$_2$OC(O)N(R$^1$)$_2$, —C(O)R$^1$ or —C(O)OC(R$^4$)(R$^5$)—OC(O)(G$^{12}$)$_m$R$^6$;
wherein $R^1$ is independently selected from the group consisting of hydrogen, substituted or unsubstituted aliphatic, and substituted or unsubstituted aryl;
wherein each $R^4$ and $R^5$ is independently selected from hydrogen, $C_1$-$C_3$ alkyl, aryl or substituted aryl;
wherein $G^{12}$ is selected from NH, CH$_2$, —S— or —O—;
wherein m is 0 or 1;
wherein $R^6$ is selected from $C_{13}$-$C_{26}$-alkyl, substituted $C_{13}$-$C_{26}$-alkyl, $C_{13}$-$C_{26}$-alkenyl, substituted $C_{13}$-$C_{26}$-alkenyl, $C_{13}$-$C_{26}$-alkynyl, substituted $C_{13}$-$C_{26}$-alkynyl, $C_{13}$-$C_{26}$-cycloalkyl, and substituted $C_{13}$-$C_{26}$-cycloalkyl, aryl-$C_{13}$-$C_{26}$-alkyl, substituted aryl-$C_{13}$-$C_{26}$-alkyl, $C_1$-$C_{10}$-aryl, substituted $C_1$-$C_{10}$-aryl, heteroaryl-$C_{13}$-$C_{26}$-alkyl, substituted heteroaryl-$C_{13}$-$C_{26}$-alkyl; optionally substituted $C_{13}$-$C_{26}$-alkylaryl, optionally substituted $C_{13}$-$C_{26}$-alkenylaryl and optionally substituted $C_{13}$-$C_{26}$-alkynylaryl; and wherein $Y^\ominus$ is a pharmaceutically acceptable counterion.

In yet another embodiment, the pharmaceutical composition has a water-insoluble antipsychotic agent that is

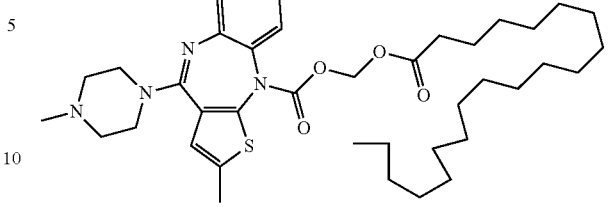

In another embodiment, the composition comprises components (a) and (b) at a ratio that results in flocs comprising component (a), wherein the flocs settle to a bed height that is greater than the sediment height of a formulation without component (b), such that components (a) and (b) can be resuspended for injection. In still another embodiment, when the composition further comprises component (d), the composition comprises components (b) and (d) at a ratio that results in flocs of component (a) wherein the flocs settle to a bed height that is greater than the sediment height of a formulation without components (b) and (d), such that components (a), (b) and (d) can be resuspended for injection.

In another embodiment, the pharmaceutical composition has a bed height that is at least a 10 to 80% increase in sediment height compared to a non-flocculated composition after 24 hours of undisturbed sitting. In other embodiments, the bed height has at least a 10 to 70, 10 to 60, 10 to 50, 10 to 40, 10 to 30 or 10 to 20% increase in sediment height compared to a non-flocculated composition after 24 hours of undisturbed sitting.

In another embodiment of the pharmaceutical composition, components (a) and (b), and optionally (d), can be resuspended for injection within 1-60 seconds of handshaking.

In an embodiment, the pharmaceutical composition contains the ratio of components (a) to (b) or the ratio of (a), (b) and (d) such that the composition can be injected using a 20 or greater gauge needle.

In still another embodiment, when the composition further comprises component (d), the ratio of components (b) to (d) is approximately 0.5-1 to 20 to 1, by weight.

In other embodiments, the pharmaceutical composition contains the ratio of components (b) to (c) that is approximately 19 to 1, 18 to 1, 17 to 1, 16 to 1, 15 to 1, 14 to 1, 13 to 1, 12 to 1, 11 to 1, 10 to 1, 9 to 1, 8 to 1, 7 to 1, 6 to 1, 5 to 1, 4 to 1, 3 to 1, 2 to 1, 1.5 to 1, 1.4 to 1, 1.3 to 1, 1.2, to 1, 1.1 to 1, 0.9 to 1, 0.8 to 1, 0.7 to 1 or 0.6 to 1 by weight.

The amount of component (b) in the pharmaceutical composition can vary. In an embodiment, the amount of component (b) in the pharmaceutical composition can be 0.1% to 20% by weight, e.g., 0.3% to 10% by weight, e.g., 0.3% to 5% by weight, e.g., 0.3% to 1% by weight. In other embodiments, the pharmaceutical composition comprises 0.1 to 19, 0.1 to 18, 0.1 to 17, 0.1 to 16, 0.1 to 15, 0.1 to 14, 0.1 to 13, 0.1 to 12, 0.1 to 11, 0.1 to 10, 0.1 to 9, 0.1 to 8, 0.1 to 7, 0.1 to 6, 0.1 to 5, 0.1 to 4, 0.1 to 3, 0.1 to 2, 0.1 to 1, 0.5 to 20, 1 to 20, 2, to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20 or 19 to 20% by weight of component (b).

As discussed above, when the pharmaceutical composition further comprises component (d), (d) can be polysorbate 20. In an embodiment, the pharmaceutical composition comprises about 0.05-1.0 weight percent polysorbate 20. In still another embodiment, the composition comprises about 0.2 weight percent polysorbate 20. In other embodiments, the pharmaceutical composition comprises about 0.1-1, 0.2-1, 0.3-1, 0.4-1, 0.5-1, 0.6-1, 0.7-1, 0.8-1, 0.9-1, 0.05-0.9, 0.05-0.8, 0.05-0.7, 0.05-0.6, 0.05-0.5, 0.05-0.4, 0.05-0.3, 0.05-0.2 or 0.05-0.1 weight percent polysorbate 20.

In another embodiment, the pharmaceutical composition has approximately 5-35, or approximately 5-15, weight percent aripiprazole, or olanzapine, or a compound of formula I, II, III, IV, V, VI, or pharmaceutically acceptable salts, hydrates, or solvates thereof.

In another aspect, provided herein is an injectable pharmaceutical composition comprising: (a) aripiprazole, or olanzapine, or a compound of formula I, II, III, IV, V, VI, or pharmaceutically acceptable salts, hydrates, or solvates thereof;
(b) sesame oil;
(c) polysorbate 20; and
(d) an aqueous carrier.

In still another aspect, provided herein is an injectable pharmaceutical composition comprising:
(a) aripiprazole, or olanzapine, or a compound of formula I, II, III, IV, V, VI, or pharmaceutically acceptable salts, hydrates, or solvates thereof.
(b) Imwitor 308; and
(c) an aqueous carrier; and
(d) optionally polysorbate 20.

In an aspect, provided herein is an injectable composition comprising a water-insoluble antipsychotic agent and sesame oil. In still another aspect, provided herein is an injectable composition comprising a water-insoluble antipsychotic agent and Imwitor 308. In an embodiment, these injectable compositions are formulated for modulating tissue reaction associated with the delivery of a water-insoluble antipsychotic agent is aripiprazole, or olanzapine, or a compound of formula I, II, III, IV, V or VI, compounds A-4 or A-7, O-56, O-111, O-112, O-7, O-8 and O-9.

In an embodiment, the injectable composition is formulated for modulating tissue reaction through a reduction in the irritation at the site of injection. In another embodiment, the injectable composition further comprises a buffer wherein the buffer is a phosphate, citrate, tartrate or acetate buffer.

In another embodiment, a method for treating disorders of the central nervous system is provided by administering an effective amount of the pharmaceutical composition to an individual in need of such treatment. In another embodiment the disorder is anxiety or depression, bipolar disorder, autism-related irritability, a psychotic condition, schizophrenia or schizophreniform diseases, or acute mania.

BRIEF DESCRIPTION OF THE FIGURES

FIG. 1 shows results from the settled bed height assessments described in the experimental section. The data indicate that pharmaceutical compositions containing sesame oil have higher settled bed heights than compositions without sesame oil.

DETAILED DESCRIPTION OF INVENTION

Pharmaceutical Compositions

Provided herein are pharmaceutical compositions comprising (a) a water-insoluble antipsychotic agent; (b) a glycerol ester of a fatty acid, wherein the fatty acid comprises 4 to 28 carbon atoms, and the glycerol ester is a mono, di, or triglyceride; and (c) an aqueous vehicle; wherein the composition forms an aqueous, flocculated, injectable suspension. The composition can comprise additional components, such as (d) a polyoxyethylene derivative of a sorbitan ester or a carboxylic acid, wherein the carboxylic acid comprises 8-20 carbon atoms (e.g., polysorbate 20). This composition is particularly useful for the formulation of a water-insoluble antipsychotic agent into an injectable pharmaceutical composition. In an embodiment, the polyoxyethylene derivative is polysorbate 20. The pharmaceutical composition can further comprise an aqueous vehicle, such as phosphate buffered saline, as well as any of the pharmaceutical components described herein.

The compositions described herein possess a number of advantages. For example, the compositions offer minimized excipient levels while co-optimizing both resuspendability and acceptable injectability, and maintain good physiochemical attributes of the antipsychotic agent. These properties can be determined based on comparisons of vehicle performance based on settled bed height and qualitative ease of resuspension. Briefly, the redispersibility of a pharmaceutical composition can be assessed by preparing a number of different formulations (antipsychotic agent with a variety of excipients), and comparing the relative height of the settled beds. In general, higher settled bed heights are indicative of flocculated, or loosely aggregated, particles. These suspensions settle faster initially, but their loosely aggregated state allows for easier redispersion and better physical stability as the particles cannot pack as tightly as fully dispersed suspensions, thereby leading to reduced resuspension times using, for example, shaking by hand. In one embodiment, the pharmaceutical compositions, e.g., a pharmaceutical composition of components (a) and (b), or (a), (b) and (c), or (a), (b), (c) and (d), can be resuspended for injection within 1-60 seconds of shaking by hand.

As used herein, the term "flocculation" refers to the formation of a loose aggregation of discrete particles held together in a network-like structure by physical adsorption of macromolecules, bridging during chemical interaction (precipitation), or when the longer range van der Waals forces of attraction exceed the shorter range forces of attraction. (See Pharmaceutical dosage forms: Disperse systems Volume 2. Edited by Herbert A. Lieberman, Martin M. Rieger, and Gilbert S. Banker. (1996) Pg. 18). The "loose aggregation of discrete particles" can be referred to herein as "flocs."

In an embodiment, the pharmaceutical compositions comprising (a) a water-insoluble antipsychotic agent and (b) a glycerol ester of a fatty acid, wherein the fatty acid comprises 4 to 28 carbon atoms, and the glycerol ester is a mono, di, or triglyceride, form a flocculated composition in the absence of an additional surfactant, such as, for example, polysorbate 20.

Accordingly, provided herein is a) a water-insoluble antipsychotic agent and (b) Imwitor, e.g., Imwitor 308. In another embodiment, an additional surfactant, such as a polyoxyethylene derivative of a sorbitan ester of a carboxylic acid, wherein the carboxylic acid comprises 8-20 carbon atoms (referred to herein as "component (d)" or "d" can be used in the formation of a flocculated solution.

Pharmaceutical compositions containing component (b) (a glycerol ester of a fatty acid, wherein the fatty acid comprises 4 to 28 carbon atoms, and the glycerol ester is a mono, di, or triglyceride) have significantly high settled bed heights, which, as described above, result in improved re-suspendability, and therefore ease of use. As shown in FIG. 1, this bed height increases as the amount of component (b) increases. As the bed height increases, the time needed for re-suspension decreases. As described below, the flocculation phenomenon is uniquely attributed to the additional influence of component (b).

Accordingly, in one embodiment, provided herein is a composition comprising components (a), (b) and (c), or (a), (b), (c) and (d), at a ratio that results in flocs, wherein the flocs settle to greater than a predetermined sediment bed height, such that components (a), (b) and (c), or components (a), (b), (c) and (d), can be resuspended for injection. The flocs can be comprised of component (a), components (a) and (b), or components (a), (b) and (d). A predetermined sediment bed height refers to a bed height that is higher than the bed height of a comparative pharmaceutical composition that has none of component (b), or none of components (b) or (d). In one embodiment, the bed height is comprised of at least a 10, 20, 30, 40, 50, 60, 70 or 80% increase in sediment height compared to a non-flocculated pharmaceutical composition after 24 hours of undisturbed sitting. In another embodiment, the bed height is comprised of at least a 10 to 80% increase in sediment height compared to a non flocculated pharmaceutical composition after 24 hours of undisturbed sitting.

In addition to the resuspendability and injectability advantages described above, the pharmaceutical compositions provided herein can result in reduced tissue reactions.

Accordingly, in one embodiment, provided herein is a method of modulating tissue reactions associated with delivering a water-insoluble antipsychotic agent into a host, comprising the water-insoluble antipsychotic agent and component (b) (a glycerol ester of a fatty acid, wherein the fatty acid comprises 4 to 28 carbon atoms). In another embodiment, the antipsychotic agent/component (b) composition is delivered to the host through a needle.

Specifically, the composition provided herein results in a decreased tissue reaction normally associated with antipsychotic agents, such as aripiprazole, olanzapine, derivatives thereof, prodrugs thereof, and salts thereof.

As used herein, the term "tissue reaction" (TR) refers to foreign body responses to a drug product (active agent and/or vehicle used for administration). For example, local tissue reaction to drug product results in the influx of immune cells, the subsequent encapsulation of the drug product and usually the development of a fluid filled central cavity. The presence of fibroblasts, neutrophils, macrophages and giant cells are often observed via histological examination. The term "undue TR" or "unacceptable TR" refers to moderate to severe TR which is unacceptable to the patient and thereby impacts unfavorably on patient comfort and compliance. The term "reduced TR" refers to generally minimal to mild TR which is acceptable to the patient and therefore does not engender an adverse event related nor impact unfavorably on patient compliance. As such, the injectable composition provided herein is characterized by a decreased undue TR and a more acceptable TR following injection of drug product. In an embodiment, a "tissue reaction" is a form of "injection site reaction."

The modulation of tissue response following SC administration is described by the reduction of the injection site weight (comprising the drug depot and surrounding tissue) which provides a quantitative assessment of the severity of the response. The modulation of the tissue response following IM administration is described by the spreadability of the drug and resulting depot morphology; spreading of the drug along the fascial planes of muscle is desirable rather than the formation of a concentrated mass of drug in a small area.

Depot morphology resulting from IM injection of aripiprazole and aripiprazole prodrugs has been described. Injections of slow-releasing formulations of drugs, including aripiprazole commonly result in the formation of "cyst-like structures", characterized by a vascularized capsule of roughly spherical shape and comprising various cell types, with or without and a central serous fluid compartment. Tissue responses to slow-releasing formulations occur as the body mounts an immune response to clear the material from the injection site; this reaction is commonly referred to as a foreign body response. The spherical nature of these reactions can result in localized discomfort and pain, as the FBR increases in size compressing on nerve fibers innervating muscle tissue and with the release of pro-inflammatory cytokines from the site.

In a particular embodiment, the modulation of the tissue reaction is the reduction in tissue reaction at the site of injection. In one embodiment, the injection site reaction is reduced by a particular amount, e.g., about 90%, 80%, 70%, 60%, 50%, 40%, 30%, 20%, 10%, 5%, etc.

When the antipsychotic agent/glycerol ester of a fatty acid (which does or does not further comprise component (d)) polyoxyethylene derivative of a sorbitan ester/benzyl alcohol composition is to be used as an injectable composition, including but not limited to injection through a needle or needle-less injection, it can be formulated into a conventional injectable carrier. Suitable carriers include biocompatible and pharmaceutically acceptable solutions.

As described above, the pharmaceutical composition comprising components (a) and (b) can comprises component (d): a polyoxyethylene derivative of a sorbitan ester of a carboxylic acid, wherein the carboxylic acid comprises 8-20 carbon atoms. In a particular embodiment, component (c) is polysorbate 20, sold under the trademark TWEEN®. The polysorbate can be added in an amount that reduces surface tension of a drug product or aids in suspension stability of the drug product.

A variety of glycerol esters of a fatty acid can be used in the pharmaceutical compositions. Generally, the fatty acid comprises 4 to 28 carbon atoms, and the glycerol ester is a mono, di, or triglyceride. In an embodiment of the pharmaceutical composition, the fatty acid comprises 6 to 20 carbon atoms, e.g., 10-19, e.g., 14-18 carbon atoms. The glycerol ester can be esters of oleic acid, linoleic acid, linolenic acid, stearic acid, palmitic acid, capric acid, lauric acid or caprylic acid, or mixtures thereof.

Furthermore, the pharmaceutical compositions can comprise one or more components that are comprised of one or more glycerol esters. Examples of such components include, but are not limited to, sesame oil, olive oil, soybean oil, coconut oil, Imwitor 308, Imwitor 742, Imwitor 312, or Imwitor 928. Because these components are the source of the glycerol esters in the pharmaceutical composition, these components themselves can be referred to as "glycerol esters", or "component (b). In a particular embodiment, the component providing a glycerol ester is sesame oil or Imwitor 308.

The amount of component (b) in the pharmaceutical composition can vary. In an embodiment, the amount of component (b) in the pharmaceutical composition can be 0.1% to 20% by weight, e.g., 0.3% to 10% by weight, e.g., 0.3% to 5% by weight, e.g., 0.3% to 1% by weight.

Provided below are representative drawings of the polyoxyethylene derivative of a sorbitan ester of a carboxylic acid used in the pharmaceutical compositions:

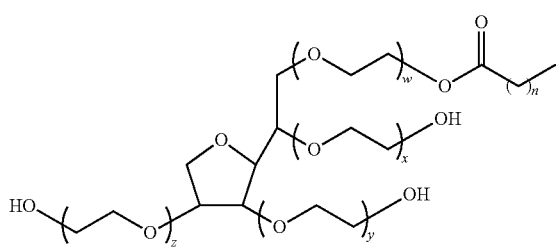

Polyoxyethylene Derivative of a Sorbitan Ester
w + x + y + z = 20
n = 6-12

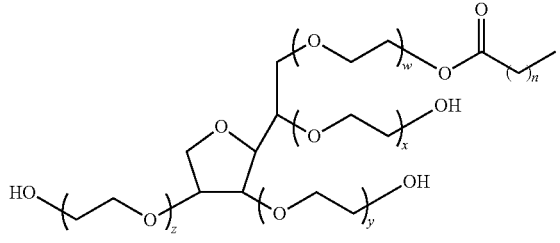

Polysorbate 20
w + x + y + z = 20
n = 10

As discussed above, the pharmaceutical compositions can form flocculated compositions in the presence of or in the absence of component (d), e.g., polysorbate 20.

For compositions comprising components (a), (b), and (d), or (a), (b), (c) and (d), the ratios of (b) and (d) can vary. In one embodiment, the ratio of components (b) to (c) is approximately 0.5-1 to 20 to 1, by weight.

In another embodiment, the composition comprises about 0.05-1.0 weight percent component (d), e.g., polysorbate 20.

In an embodiment, the ratio of components (b) to (c) is such that the composition can be injected using a 20-25 gauge needle. For example, the needle can be a 20, 21, or 23.5 gage needle.

The compositions provided herein can also have varying amounts of antipsychosis agent. The antipsychosis agent can be aripiprazole, or olanzapine, salts of these compounds, hydrates of these compounds, and/or prodrugs of these compounds. In one embodiment, the composition comprises approximately 1-35 weight percent aripiprazole, or olanzapine, or a compound of formula I, II, III, IV, V or VI (lurasidone), or pharmaceutically acceptable salts, hydrates, or solvates thereof. In another embodiment, the composition comprises approximately 5-15 weight percent aripiprazole, or olanzapine, or a compound of formula I, II, III, IV, V or VI, or pharmaceutically acceptable salts, hydrates, or solvates thereof. In still another embodiment, the composition comprises approximately 10 weight percent aripiprazole, aripiprazole, or olanzapine, or a compound of formula I, II, III, IV, V or VI, or pharmaceutically acceptable salts, hydrates, or solvates thereof. In another embodiment, the composition comprises approximately 24-26 weight percent aripiprazole, or olanzapine, or a compound of formula I, II, III, IV, V or VI, or pharmaceutically acceptable salts, hydrates, or solvates thereof. In another embodiment, the composition comprises approximately 15-35, e.g., 18-26, e.g., 20-24, e.g., approximately 22 weight percent aripiprazole, or olanzapine, or a compound of formula I, II, III, IV, V or VI, or pharmaceutically acceptable salts, hydrates, or solvates thereof.

The aqueous vehicle of the pharmaceutical compositions provided herein can be a buffer. The buffer may be selected from a phosphate, citrate, tartrate or acetate buffer. In a particular embodiment, the buffer is a phosphate buffer.

The pharmaceutical compositions provided herein can further comprise additional components. For example, the use of additional wetting agents or surfactants in a pharmaceutical composition may promote one or more of the following:

(1) Surface tension reduction, which may aid in wetting, since a 'lower surface tension' liquid will wet surfaces or particles more readily than a 'high surface tension' liquid. Lowering the surface tension of a liquid may also decrease the incidence of foaming. The surface tension of a liquid will be lower as more surfactant is added;

(2) Formation of micelles (i.e., spherical or non-spherical surfactant structures in solution that have the capability to dissolve non-soluble components); and/or (3) Increase of suspension physical stability.

The pharmaceutical compositions can also contain an aqueous vehicle, which is a vehicle that dilutes and suspends the drug. The diluent of interest herein is one which is pharmaceutically acceptable (safe and non-toxic for administration to a human) and is useful for the preparation of a reconstituted formulation. Exemplary diluents include sterile water, sterile water for injection (WFI), bacteriostatic water for injection (BWFI), a pH buffered solution (e.g., phosphate-buffered saline), sterile saline solution, Ringer's solution or dextrose solution. The buffer can be phosphate, citrate, tartrate or acetate. In a particular embodiment, the diluent is phosphate-buffered saline, which is a water-based salt solution containing either sodium chloride or potassium chloride, and sodium phosphate or potassium phosphate. In one embodiment, the phosphate buffer comprises isotonic saline with 5-50 mM phosphate buffer at pH 4.0-9.0, e.g., 5.0-8.0, e.g., 5.0-7.5.

The pharmaceutical compositions can further contain an additional surfactant that preferentially adsorbs to an interface between two immiscible phases, such as the interface between water and an organic polymer solution, a water/air interface or organic solvent/air interface. Suitable surfactants include but are not limited to fatty alcohols such as polyethylene glycols (PEGs) and cetyl alcohol.

Optionally, the pharmaceutical compositions can further comprise a dispersant, such as, for example, carboxymethyl cellulose (CMC), carboxymethyl cellulose sodium, cross-linked sodium carboxymethyl cellulose, calcium carboxymethyl cellulose, and low substituted hydroxypropyl cellulose magnesium aluminum silicate, or a mixture thereof. In a particular embodiment, the pharmaceutical composition comprises carboxymethyl cellulose.

The pharmaceutical compositions may also optionally comprise an antioxidant to inhibit the oxidation of ingredients. Some examples of antioxidants include, but are not limited to, ascorbic acid, ascorbyl palmitate, butylated hydroxyanisole, a mixture of 2 and 3 tertiary-butyl-4-hydroxyanisole, butylated hydroxytoluene, sodium iso-ascorbate, dihydroguaretic acid, potassium sorbate, sodium bisulfate, sodium metabisulfate, sorbic acid, potassium ascorbate, vitamin E, 4-chloro-2,6-ditertiary butylphenol, alpha-tocopherol, and propylgallate.

The pharmaceutical compositions can further include a lipid, e.g., a neutral lipid. Neutral lipids include any lipid that remains neutrally charged at a pH between about 4 and 9. Neutral lipids include, without limitation, cholesterol, other sterols and derivatives thereof, phospholipids, and combinations thereof and other neutral lipids. The phospholipids include any one phospholipid or combination of phospholipids capable of forming liposomes. They include phosphatidylcholines, phosphatidylethanolamines, lecithin and fractions thereof, phosphatidic acid, phosphatidylglycerols, phosphatidylinositols, phosphatidylserines, plasmalogens and sphingomyelins. The phosphatidylcholines include, without limitation, those obtained from egg, soy beans or other plant sources or those that are partially or wholly synthetic or of variable lipid chain length and unsaturation, POPC, OPPC, natural or hydrogenated soy bean PC, natural or hydrogenated egg PC, DMPC, DPPC, DSPC, DOPC and derivatives thereof. In one embodiment, phosphatidylcholines are POPC, non-hydrogenated soy bean PC and non-hydrogenated egg PC. Phosphatidylethanolamines include, without limitation, DOPE, DMPE and DPPE and derivatives thereof. Phosphatidylglycerols include, without limitation, DMPG, DLPG, DPPG, and DSPG. Phosphatidic acids include, without limitation, DSPA, DMPA, DLPA and DPPA.

The pharmaceutical compositions can also advantageously employ a density enhancing agent, such as a sugar, e.g., mannitol, or sorbitol and/or a tonicity adjusting agent, such as sodium chloride or glycerol.

Other pharmaceutical carriers that could be used in the pharmaceutical compositions provided herein also include water, aqueous methylcellulose solutions, saline, dextrose solutions, fructose solutions, ethanol, or oils of animal, vegetative, or synthetic origin. The pharmaceutical carrier may also contain preservatives, and buffers as are known in the art.

The term "pharmaceutical composition", "formulation", "injectable composition," etc. are used synonymously throughout the application.

The pharmaceutical compositions described herein may also be in the form of an emulsion. The term "emulsion" as used in this specification denotes a two-phase system in which one phase is finely dispersed in the other phase. An emulsifier can be used in the pharmaceutical compositions to form the emulsion. The term emulsifier, as used by this invention, denotes an agent that can reduce and/or eliminate the surface and the interfacial tension in a two-phase system. Such an agent possesses both hydrophilic and lipophilic groups in the emulsifier agent.

The pharmaceutical compositions described herein may also be in the form of a dispersion. As used herein, the term "dispersion" is to be understood as a mixture in which fine particles of one substance (e.g., a drug) are scattered throughout another substance (e.g., a liquid). Dispersions include suspensions, and colloids.

The methods of the invention include administering the compositions described herein, thereby obtaining an extended release or sustained release profile in the patient. "Extended-release" or "sustained-release" includes dosage forms whose drug-release characteristics of time course and/or location are chosen to accomplish therapeutic or convenience objectives not offered by conventional dosage forms such as a solution or an immediate release dosage form. An extended release profile includes deliveries that achieve a therapeutically effective amount of the antipsychotic agent, e.g., aripiprazole, or olanzapine, or a compound of formula I, II, III, IV, V or VI, is present in the plasma of the individual for at least about 7 days, preferably at least about 14 days, or more preferably at least about 21 days alternatively for at least 2, 3, 4, 6 or 8 weeks or as much as three months.

In one embodiment, the pharmaceutical compositions can be administered as a single or sole (undivided) dose. However, the composition is also useful for those individuals that require constant or chronic therapy, such as those that receive repeated doses over several hours, days, weeks, months, or more. In such dosing regimens, the method can comprise a first administration of a first extended release composition and a second administration of a second extended release composition. The second composition can be the same, substantially the same or different as the first and can include the same active agent or a different active agent. For example, the second composition can be administered at about 7 days, or more, such as at least about 14 days, or at least about 17 days, after the first administration, where the first administration results in the release of agent for a period of 1, 2, 3, 4, 5, 6, 7, 8, 9, 10, 11, 12, 13, 14 days, or more.

The injectable, pharmaceutical compositions described herein can be injected into a patient in any number of ways. The term "injectable" as used herein refers to a composition that is suitable to be delivered to an individual in an injection, such as with an injection device, including one that employs a syringe or a cartridge, which may be housed in a manual injection device or an auto-injection device, for example. Specifically, the injectable composition is suitable for parenteral administration. As used herein, the term "parenteral administration" refers to administration through injection or infusion. Parenteral administration includes, but is not limited to, intravenous administration, intradermal administration, subcutaneous administration or intramuscular administration. The term "intravenous administration" means administration into a vein. "Intradermal administration" is injection into the upper layer of skin (i.e., the dermis), just beneath the epidermis. "Subcutaneous administration" refers to administration just below the skin. "Intramuscular administration" is the injection directly into a muscle.

Accordingly, in one aspect, provided herein is an injectable pharmaceutical composition comprising:
  (a) aripiprazole, or olanzapine, or a compound of formula I, II, III, IV, V, VI, or pharmaceutically acceptable salts, hydrates, or solvates thereof;
  (b) sesame oil;
  (c) polysorbate 20; and
  (d) an aqueous carrier.

In another aspect, provided herein is an injectable pharmaceutical composition comprising:
  (a) aripiprazole, or olanzapine, or a compound of formula I, II, III, IV, V, VI, or pharmaceutically acceptable salts, hydrates, or solvates thereof;
  (b) Imwitor 308; and
  (c) an aqueous carrier; and
  (d) optionally polysorbate 20.

In still another aspect, provided herein is an injectable pharmaceutical composition comprising:
  (a) aripiprazole, or olanzapine, or a compound of formula I, II, III, IV, V, VI, or pharmaceutically acceptable salts, hydrates, or solvates thereof in a weight ratio of approximately 5-35%;
  (b) a glycerol ester of a fatty acid, wherein the fatty acid comprises 4 to 28 carbon atoms, wherein the glycerol ester is a mono, di, or triglyceride in a weight ratio of approximately 0.3-20%;
  (c) polysorbate 20 in a weight ratio of approximately 0-1%; and
  (d) an aqueous carrier.

In another aspect, provided herein is an injectable pharmaceutical composition comprising:
(a) aripiprazole, or olanzapine, or a compound of formula I, II, III, IV, V, VI, or pharmaceutically acceptable salts, hydrates, or solvates thereof in a weight ratio of approximately 5-15%;
(b) a glycerol ester of a fatty acid, wherein the fatty acid comprises 4 to 28 carbon atoms, wherein the glycerol ester is a mono, di, or triglyceride in a weight ratio of approximately 0.3-20%;
(c) polysorbate 20 in a weight ratio of approximately 0-1%; and
(d) an aqueous carrier.

In yet another aspect, provided herein is an injectable pharmaceutical composition comprising:
(a) aripiprazole, or olanzapine, or a compound of formula I, II, III, IV, V, VI, or pharmaceutically acceptable salts, hydrates, or solvates thereof in a weight ratio of approximately 5-15%;
(b) a glycerol ester of a fatty acid, wherein the fatty acid comprises 4 to 28 carbon atoms, wherein the glycerol ester is a mono, di, or triglyceride in a weight ratio of approximately 0.3-5%;
(c) polysorbate 20 in a weight ratio of approximately 0-1%; and
(d) an aqueous carrier.

In another aspect, provided herein is an injectable pharmaceutical composition comprising:
(a) aripiprazole, or olanzapine, or a compound of formula I, II, III, IV, V, VI, or pharmaceutically acceptable salts, hydrates, or solvates thereof in a weight ratio of approximately 5-35%;
(b) a glycerol ester of a fatty acid, wherein the fatty acid comprises 4 to 28 carbon atoms, wherein the glycerol ester is a mono, di, or triglyceride in a weight ratio of approximately 0.3-5%;
(c) polysorbate 20 in a weight ratio of approximately 0-1%; and
(d) an aqueous carrier.

In one embodiment, provided herein is an injectable pharmaceutical composition comprising:
(a) olanzapine, Compound O-7, Compound O-8, or Compound O-9, in a weight ratio of approximately 5-35%;
(b) sesame oil in a weight ratio of approximately 0.3-20%;
(c) polysorbate 20 in a weight ratio of approximately 0-1%; and
(d) an aqueous carrier.

In another embodiment, provided herein is an injectable pharmaceutical composition comprising:
(a) olanzapine, Compound O-7, Compound O-8, or Compound O-9, in a weight ratio of approximately 5-15%;
(b) sesame oil in a weight ratio of approximately 0.3-20%;
(c) polysorbate 20 in a weight ratio of approximately 0-1%; and
(d) an aqueous carrier.

In yet another embodiment, provided herein is an injectable pharmaceutical composition comprising:
(a) olanzapine, Compound O-7, Compound O-8, or Compound O-9, in a weight ratio of approximately 5-15%;
(b) sesame oil in a weight ratio of approximately 0.3-5%;
(c) polysorbate 20 in a weight ratio of approximately 0-1%; and
(d) an aqueous carrier.

In another embodiment, provided herein is an injectable pharmaceutical composition comprising:
(a) olanzapine, Compound O-7, Compound O-8, or Compound O-9, in a weight ratio of approximately 5-35%;
(b) sesame oil in a weight ratio of approximately 0.3-5%;
(c) polysorbate 20 in a weight ratio of approximately 0-1%; and
(d) an aqueous carrier.

Antipsychotic Agents

As discussed above, the pharmaceutical compositions provided herein are useful for the administration of antipsychotic drugs to a subject. As used herein the term "antipsychotic" refers all drugs used to treat psychosis. Common conditions for which antipsychotics are prescribed include schizophrenia, mania and delusional disorder, although antipsychotics are also used to counter psychosis associated with a wide range of other diagnoses. Antipsychotics also act as mood stabilizers making them suitable for the treatment of bipolar disorder (even when no symptoms of psychosis are present). The pharmaceutical compositions provided herein are particularly useful for formulating a water-insoluble antipsychotic into an injectable composition.

The pharmaceutical compositions described herein are useful for administration of water-insoluble antipsychotic agents. As used herein, a water-insoluble antipsychotic agent is one that dissolves in a quantity of water to an extent of less than 100%. The term "water-insoluble" does not necessarily refer to complete or 100% water-insolubility. In certain embodiments, the water-insoluble material dissolves to an extent of less than 50%. In other embodiments, the water-insoluble material dissolves to an extent of less than 10%. In a particular embodiment, the water-insoluble material dissolves to an extent of less than 1%. The term "water-insoluble" can refer to solubility as prescribed in the United States Pharmacopoeia.

In one embodiment, the antipsychotic drug of the pharmaceutical composition is aripiprazole. The aripiprazole drug substance can comprise, consist essentially of, or consist of aripiprazole (in a crystalline, non-crystalline or amorphous form), an aripiprazole salt, an aripiprazole solvate (including ethanolates and hydrates), or other aripiprazole polymorphs. Preferred salts include those salts insoluble in an aqueous vehicle. Pharmaceutical salts such as the hydrochloride and various pharmaceutically acceptable carboxylate salts are suitable.

The aripiprazole drug substance can also include aripiprazole prodrugs. The term "prodrug" is art-recognized and is intended to encompass compounds which, under physiological conditions, are converted into active compounds, e.g., those described herein. A common method for making a prodrug is to select moieties which are hydrolyzed or otherwise cleaved under physiological conditions to provide the desired compound. In other embodiments, the prodrug is converted by an enzymatic activity of the host animal.

Preferred aripiprazole prodrugs that can be used in the pharmaceutical compositions include the prodrugs described in U.S. Publication No. 2011/0003828, which is incorporated herein by reference in its entirety.

In a particular embodiment, the aripiprazole prodrug is a compound of formula (I) or formula (II):

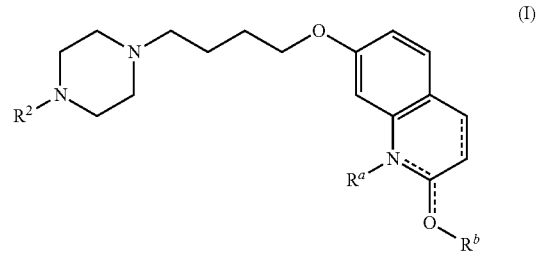

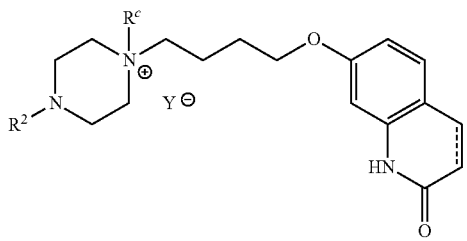

(II)

wherein
R$^a$ is absent, and R$^b$ is —CH$_2$OC(O)R$^1$, —CH$_2$OC(O)OR$^1$, —CH$_2$OC(O)N(R$^1$)$_2$ or —C(O)R$^1$;
or
R$^b$ is absent, and R$^a$ is —CH$_2$OC(O)R$^1$, —CH$_2$OC(O)OR$^1$, —CH$_2$OC(O)N(R$^1$)$_2$ or —C(O)R$^1$;
R$^c$ is —CH$_2$OC(O)R$^1$, —CH$_2$OC(O)OR$^1$, —CH$_2$OC(O)N(R$^1$)$_2$ or —C(O)R$^1$;
wherein each R$^1$ is independently selected from the group consisting of hydrogen, substituted or unsubstituted aliphatic, and substituted or unsubstituted aryl; and
wherein each R$^2$ is selected from the group consisting of substituted or unsubstituted aryl and substituted or unsubstituted heteroaryl;
wherein Y$^\ominus$ is a pharmaceutically acceptable counterion; and
wherein ========= represents a single or double bond.
Suitable counterions include, e.g., chloride, bromide, iodide, sulfate, phosphate, acetate, benzoate, tartrate, citrate, propionate, gluconate, lactate, maleate, fumarate, camsylate, glucepate, mesylate, napsylate, pamoate, conjugate bases of organic carboxylic acids, and the like.
In one embodiment of formula (I), the aripiprazole prodrug is a compound of formula (I'):

(I')

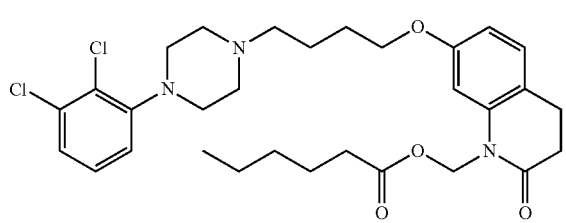

wherein R$^a$ is CH$_2$OC(O)R$^1$ and wherein R$^1$ is selected from substituted or unsubstituted aliphatic.
In a particular embodiment of formula (I'), R$^1$ is —CH$_2$OC(O)—(CH$_2$)$_4$CH$_3$ (Compound A-4). In another particular embodiment of formula (I'), R$^1$ is —CH$_2$OC(O)—(CH$_2$)$_{10}$CH$_3$ (Compound A-7). Compounds A-4 and A-7 are depicted below:

A-4

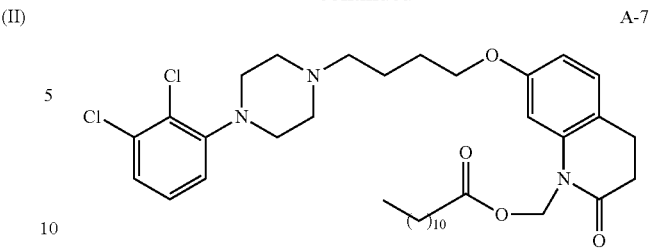

A-7

In another embodiment, the antipsychotic drug of the pharmaceutical composition is olanzapine. The olanzapine drug substance can comprise, consist essentially of, or consist of olanzapine (in a crystalline, non-crystalline or amorphous form), an olanzapine salt, an olanzapine solvate (including for example ethanolates and hydrates), or other olanzapine polymorphs. A preferred olanzapine salt is olanzapine pamoate. The antipsychotic drug can also be an olanzapine prodrug.
The olanzapine drug substance can also include olanzapine prodrugs of Formula (III), (IV) or (V):

(III)

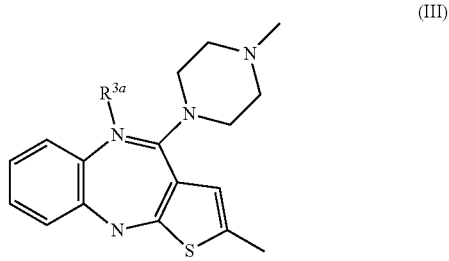

(IV)

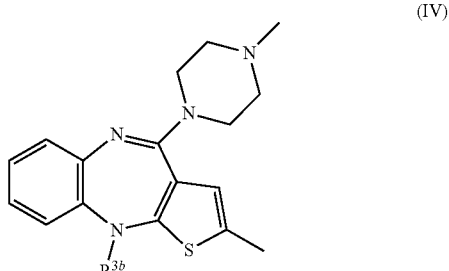

(V)

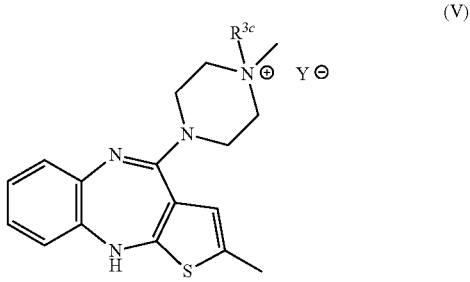

wherein R$^{3a}$, R$^{3b}$, and R$^{3c}$ are independently —CH$_2$OC(O)R$^1$, —CH$_2$OC(O)OR$^1$, —CH$_2$OC(O)N(R$^1$)$_2$, —C(O)R$^1$ or —C(O)OC(R$^4$)(R$^5$)—OC(O)(G$^{12}$)$_m$R$^6$;
wherein R$^1$ is independently selected from the group consisting of hydrogen, substituted or unsubstituted aliphatic, and substituted or unsubstituted aryl;
wherein each R$^4$ and R$^5$ is independently selected from hydrogen, C$_1$-C$_3$ alkyl, aryl or substituted aryl; preferably, hydrogen or methyl;

wherein $G_{12}$ is selected from NH, $CH_2$, —S— or —O—; wherein m is 0 or 1;

wherein $R^6$ is selected from $C_{13}$-$C_{26}$-alkyl, substituted $C_{13}$-$C_{26}$-alkyl, $C_{13}$-$C_{26}$-alkenyl, substituted $C_{13}$-$C_{26}$-alkenyl, $C_{13}$-$C_{26}$-alkynyl, substituted $C_{13}$-$C_{26}$-alkynyl, $C_{13}$-$C_{26}$-cycloalkyl, and substituted $C_{13}$-$C_{26}$-cycloalkyl, aryl-$C_{13}$-$C_{26}$-alkyl, substituted aryl-$C_{13}$-$C_{26}$-alkyl, $C_1$-$C_{10}$-aryl, substituted $C_1$-$C_{10}$-aryl, heteroaryl-$C_{13}$-$C_{26}$-alkyl, substituted heteroaryl-$C_{13}$-$C_{26}$-alkyl; optionally substituted $C_{13}$-$C_{26}$-alkylaryl, optionally substituted $C_{13}$-$C_{26}$-alkenylaryl and optionally substituted $C_{13}$-$C_{26}$-alkynylaryl; and wherein $Y^\ominus$ is a pharmaceutically acceptable counterion.

Suitable counterions include, e.g., chloride, bromide, iodide, sulfate, phosphate, acetate, benzoate, tartrate, citrate, propionate, gluconate, lactate, maleate, fumarate, camsylate, glucepate, mesylate, napsylate, pamoate, conjugate bases of organic carboxylic acids, and the like.

In one embodiment of formula (III), $R^{3a}$ is —C(O)OCH$_2$OC(O)R$^6$ and $R^6$ is selected from $C_{13}$-$C_{26}$-alkyl. In a particular embodiment of formula (III), $R^{3a}$ is —C(O)OCH$_2$OC(O)(CH$_2$)$_{14}$CH$_3$ (Compound O-56). In another particular embodiment of formula (III), $R^{3a}$ is —C(O)OCH$_2$OC(O)(CH$_2$)$_{16}$CH$_3$ (Compound O-111). In still another particular embodiment of formula (III), $R^{3a}$ is —C(O)OCH$_2$OC(O)(CH$_2$)$_{18}$CH$_3$ (Compound O-112). Compounds O-56, O-111 and O-112 are depicted below:

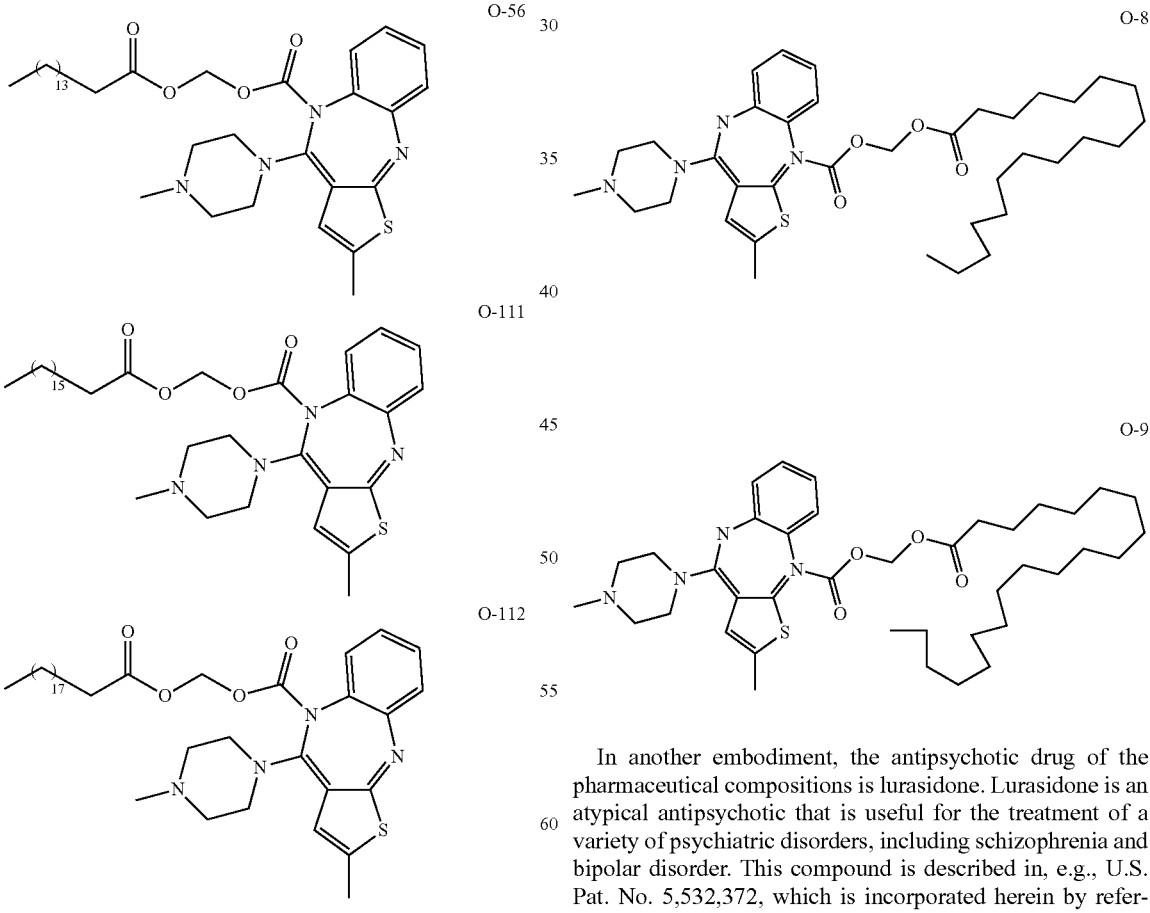

In one embodiment of formula (IV), $R^{3b}$ is —C(O)OCH$_2$OC(O)R$^6$ and $R^6$ is selected from $C_{13}$-$C_{26}$-alkyl. In a particular embodiment of formula (IV), $R^{3b}$ is —C(O)OCH$_2$OC(O)(CH$_2$)$_{14}$CH$_3$ (Compound O-7). In another particular embodiment of formula (IV), $R^{3b}$ is —C(O)OCH$_2$OC(O)(CH$_2$)$_{16}$CH$_3$ (Compound O-8). In still another particular embodiment of formula (IV), $R^{3b}$ is —C(O)OCH$_2$OC(O)(CH$_2$)$_{18}$CH$_3$ (Compound O-9). Compounds O-7, O-8 and O-9 are depicted below:

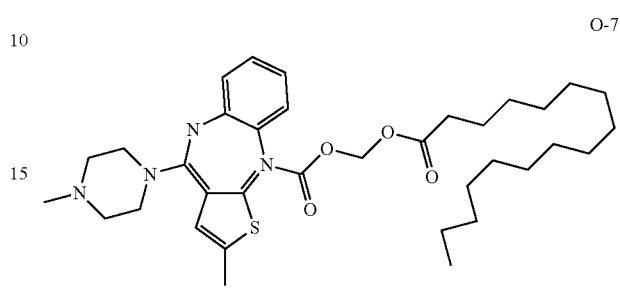

In another embodiment, the antipsychotic drug of the pharmaceutical compositions is lurasidone. Lurasidone is an atypical antipsychotic that is useful for the treatment of a variety of psychiatric disorders, including schizophrenia and bipolar disorder. This compound is described in, e.g., U.S. Pat. No. 5,532,372, which is incorporated herein by reference. Lurasidone is the generic name of the compound (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione:

(VI)

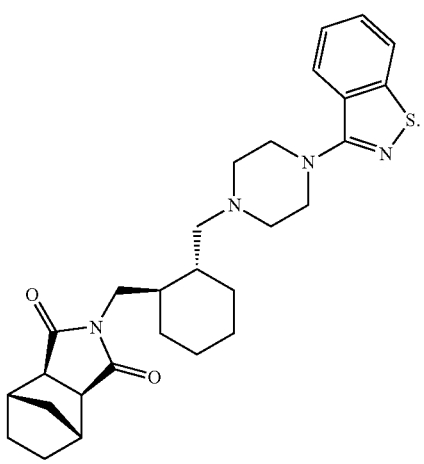

The lurasidone drug substance can comprise, consist essentially of, or consist of lurasidone free base (in a crystalline, non-crystalline or amorphous form), a lurasidone salt, a lurasidone solvate (including for example ethanolates and hydrates), or other lurasidone polymorphs. The lurasidone drug substance can also include lurasidone prodrugs.

Accordingly, aripiprazole, or olanzapine, or a compound of formula I, II, III, IV, V or VI can be referred to as an "antipsychotic agent."

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted.

An aliphatic group, when used as a linker, preferably contains between about 1 and about 24 atoms, more preferably between about 4 to about 24 atoms, more preferably between about 4 to about 12 atoms, more typically between about 4 and about 8 atoms. An aliphatic group, when used as a substituent, preferably contains between about 1 and about 30 atoms, more preferably between about 4 to about 19 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

In certain embodiments, the aliphatic groups of the present invention are alkyl chains containing from 5 to 11 carbon atoms. In other embodiments, the aliphatic groups are alkyl chains containing from 15 to 19 carbon atoms.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. In an embodiment, aryl is unsubstituted or independently substituted one or more times with halogen, $C_{1-6}$ alkyl, or O—$C_{1-6}$ alkyl.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "compound" is defined herein to include pharmaceutically acceptable salts, solvates, hydrates, polymorphs, enantiomers, diastereoisomers, racemates and the like of the compounds having a formula as set forth herein.

Methods of Treatment

The pharmaceutical compositions provided herein can be used for treatment of a variety of disorders in a subject in need thereof. For example, the disclosed compositions may be used to treat conditions selected from: disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), attention deficit disorder (ADD), attention deficit hyperactivity disorder (ADHD), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

In another embodiment, the present invention provides a method of treating cardiac and cardiovascular disorders such as angina, arrhythmia, and hypertension, in a patient in need thereof. The method comprises administering to the subject a therapeutically effective amount of a composition of the invention or a pharmaceutically acceptable salt thereof.

The invention further relates to the treatment of fever, diabetes, allergy, asthma, infection, inflammation, and ulcers in a patient in need thereof, comprising administering to the subject a therapeutically effective amount of a composition of the invention or a pharmaceutically acceptable salt thereof.

The invention further relates to the treatment of sleep modulation comprising administration of a composition of the invention. Sleep modulation includes decreasing the time to sleep onset, increasing the average sleep bout length, and increasing the maximum sleep bout length.

In a particular embodiment, the pharmaceutical compositions described herein can be used to treat anxiety, depression, bipolar disorder, autism-related irritability, and psychotic conditions including acute mania, schizophrenia and schizophreniform diseases in a subject.

The term "treated," "treating" or "treatment" includes the diminishment or alleviation of at least one symptom associated with psychosis or a related CNS disorder. The term "treated," "treating" or "treatment" as used in reference to a disease or condition shall mean to intervene in such disease or condition so as to prevent or slow the development of, prevent or slow the progression of, halt the progression of, or eliminate the disease or condition.

As used herein, the term "modulating" or "modulate" refers to an effect of altering a biological activity, especially a biological activity associated with an injection site reaction.

The term "subject" is intended to include animals, which are capable of suffering from or afflicted with dementia associated with psychosis or a related CNS disorder, including, without limitation, psychotic conditions including acute mania, schizophrenia and schizophreniform disorders, bipolar disorder, anxiety and depression. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from any of the diseases described herein.

The term "about" or "approximately" usually means within 20%, more preferably within 10%, and most preferably still within 5% of a given value or range. Alternatively, especially in biological systems, the term "about" means within about a log (i.e., an order of magnitude), preferably within a factor of two of a given value.

In one embodiment, a therapeutically effective amount of the agent is given to a subject using the pharmaceutical compositions provided herein. The term "therapeutically effective amount" is further meant to define an amount resulting in the improvement of any parameters or clinical symptoms. The actual dose may vary with each patient and does not necessarily indicate a total elimination of all disease symptoms. In the case of antipsychotics, the management of exacerbations and maintenance of remission of psychiatric symptoms are main goals of therapy, and selection of the appropriate drug and dosage in a particular disease balances these goals with the minimization of adverse events attributable to the drug.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Preferred suitable dosages for the compounds used in the treatment described herein are on the order of about 1 mg to about 600 mg, preferably about 3, 5, 10, 15, 20, 25, 30, 35, 40, 45, 50, 55, 60, 65, 70, 75, 80, 90, 95, 100, 120, 140, 160, 180, 200, 220, 240, 260, 280, 300, 320, 340, 360, 380, 400, 420, 440, 460, 480, 500, 520, 540, 560, 580 to about 600 mgs total of active. Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition used in the treatment described herein can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth. Unit dose preparations provided herein can contain aripiprazole, a compound of Formula I or a compound of Formula II in the range of about 60 to about 800 mgs (aripiprazole base equivalents). Unit dose preparations provided herein can contain olanzapine, a compound of Formula III, a compound of Formula IV or a compound of Formula V in the range of 40 to about 500 mgs (olanzapine base equivalents). Unit dose preparations provided herein can contain a compound of Formula VI in the range of 160 to about 1000 mgs (lurasidone base equivalents).

Preferred amounts according to the selected mode of administration are able to be determined by one skilled in the art. Pharmaceutical compositions can be manufactured utilizing techniques known in the art. Typically the therapeutically effective amount of the compound will be admixed with a pharmaceutically acceptable carrier.

EXEMPLIFICATION OF THE INVENTION

The invention is further illustrated by the following examples and prophetic examples. These examples and prophetic examples should not be construed as further limiting.

Example I—Formulation Optimization of Antipsychotic Drug Product

As shown in FIG. 1, pharmaceutical compositions containing component (b) (e.g., sesame oil) have significantly higher settled bed heights than compositions without component (b). The samples in the photo are for 10% drug load by weight of Compound O-7 in 0.2% aqueous polysorbate 20 with: (left) 0.5% sesame oil, (center) no additional additives, (right) 0.5% sorbitan laurate. After initial preparation, all suspensions were allowed to stand for four days and then lined up in front of a black screen and photographed.

The sesame oil and polysorbate 20 vials were resuspended by repeatedly inverting. The control (polysorbate 20 alone) required about 30-35 inversion cycles over 60-70 seconds. The sesame oil sample required only 7-8 inversion cycles over 14-16 seconds.

Example II—Prodrug Synthesis Procedures

Synthesis of Aripiprazole Prodrugs

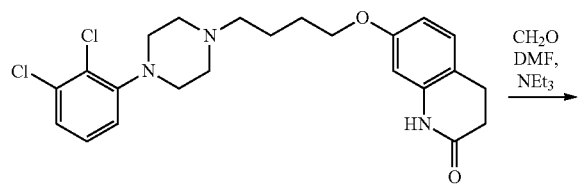
Aripiprazole

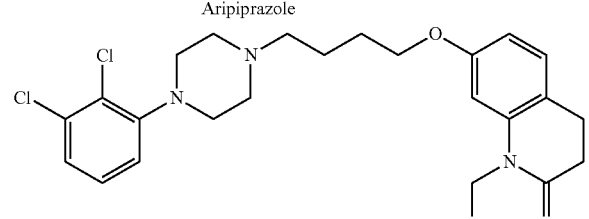
Example 1

Compound A-1: Preparation of 7-(4-(4-(2,3-dichlorophenyl)piperazin-1-yl)butoxy)-1-(hydroxymethyl)-3,4-dihydroquinolin-2(1H)-one A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over MgSO$_4$, filtered and evaporated to dryness under vacuum to give hemi-aminal A-1 as a white solid (18.6 g, containing 25% Aripiprazole, 65% yield based on A-1).

Compound 1: (7-(4-(4-(2,3-dichlorophenyl)piperazin-1-yl)butoxy)-2-oxo-3,4-dihydroquinolin-1(2H)-yl)methyl acetate

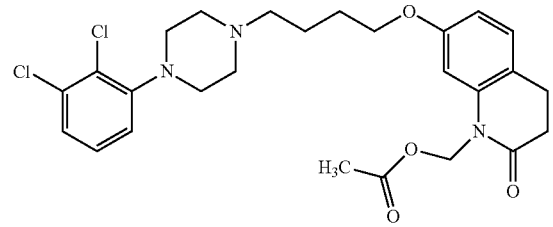 [SMILES: CC(=O)OCN1C(=O)CCc2ccc(OCCCCN3CCN(c4cccc(Cl)c4Cl)CC3)cc21]

A solution of Compound A-1 (50.63 g, 0.105 mol) in anhydrous tetrahydrofuran (THF, 80 mL) was treated with acetic anhydride (15.3 mL, 0.16 mol) and heated for 2.0 hours at 60° C. (oil-bath). To the above solution, triethylamine (2.0 mL, 0.014 mol) was added and stirred for 16 hours at 60° C. The solvent was removed using a rotator evaporator. To the resulting crude mixture, ethyl acetate (150 mL) and heptane (50 mL) was added. The solution was washed with NaHCO$_3$ (5% aqueous solution, 250 mL). After separation of the two layers, pH of the aqueous layer was adjusted to above 7. The aqueous layer was further extracted using the organic mixture. The organic layer was separated and washed with 5% NaHCO$_3$ solution, followed by deionized water, and brine. The solution was dried using anhydrous MgSO$_4$, filtered and evaporated under vacuum. The resulting product was purified using silica gel column chromatography using ethanol:ethyl acetate (5:95) as the eluent. Fractions containing the desired product were combined and d-tartaric acid (12.5 g dissolved in 60:5 ethanol:water) was added, resulting in the precipitation of the desired product (48.78 g, 89% yield). $^1$H NMR (CDCl$_3$, 300 MHz) δ 1.73 (m, 2H), 1.84 (m, 2H), 2.12 (s, 3H), 2.50 (t, 2H), 2.68 (m, 6H), 2.87 (dd, 2H), 3.08 (m, 4H), 3.98 (t, 2H), 5.91 (s, 2H), 6.59 (m, 2H), 6.96 (dd, 1H), 7.08 (dd, 1H), 7.15 (m, 2H).

Compound A-7: (7-(4-(4-(2,3-dichlorophenyl)piperazin-1-yl)butoxy)-2-oxo-3,4-dihydroquinolin-1(2H)-yl)methyl dodecanoate

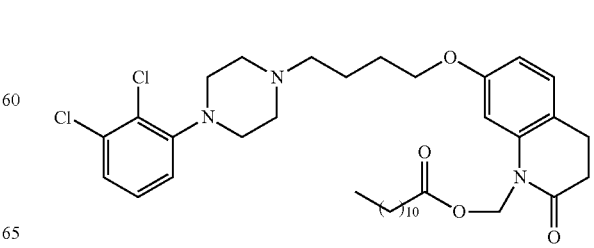

Compound A-7 was prepared in an analogous fashion to Compound 1. The desired product was isolated as a crystalline solid (0.3 g, 21% yield). The molecular weight was confirmed by mass spectrometer analysis. $^1$H NMR (CDCl$_3$, 300 MHz) δ 0.87 (t, 3H), 1.24 (m, 16H), 1.62 (m, 2H), 1.83 (m, 2H), 1.86 (m, 2H), 2.36 (t, 2H), 2.49 (t, 2H), 2.68 (m, 6H), 2.86 (dd, 2H), 3.08 (m, 4H), 3.97 (t, 2H), 5.91 (s, 2H), 6.59 (m, 2H), 6.96 (dd, 1H), 7.07 (dd, 1H), 7.14 (m, 2H).

Compound A-28: (7-(4-(4-(2,3-dichlorophenyl)piperazin-1-yl)butoxy)-2-oxo-3,4-dihydroquinolin-1(2H)-yl)methyl benzylcarbamate

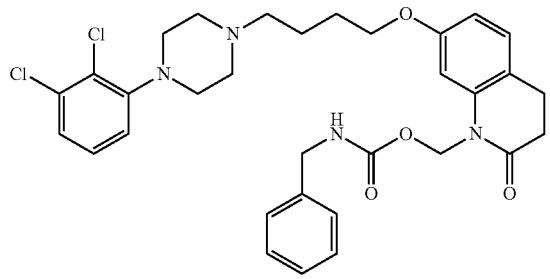 [SMILES: O=C(NCc1ccccc1)OCN1C(=O)CCc2ccc(OCCCCN3CCN(c4cccc(Cl)c4Cl)CC3)cc21]

To a solution of hemi-aminal A1 (4 g, 8.4 mmol), 4-dimethylaminopyridine (0.15 g, 1.3 mmol) and triethylamine (1.1 mL, 7.5 mmol) in dichloromethane (30 mL) was added benzylisocyanate (1.03 mL, 8.3 mmol) and the reaction mixture stirred for 24 hours. The reaction mixture was then heated at 35° C. for 20 hours, cooled and washed with water/brine (1:1, 50 mL). The organic phase was dried over MgSO$_4$, filtered and evaporated under vacuum. The residue was further purified by chromatography on silica eluting with ethyl acetate/dichloromethane/methanol (1:1:0.1) to give the desired product as an off white foam (530 mg, 14% yield). $^1$H NMR (CDCl$_3$, 300 MHz) δ 1.58-1.88 (m, 4H), 2.48 (t, 2H), 2.60-2.72 (m, 6H), 2.85 (m, 2H), 300-3.12 (m, 4H), 3.96 (t, 2H), 4.40 (d, 2H), 5.13 (NH), 5.96 (s, 2H), 6.58 (dd, 1H), 6.79 (d, 1H), 6.92-6.98 (m, 1H), 7.04 (d, 1H), 7.12-7.16 (m, 1H), 7.23-7.35 (m, 6H); m/z (M$^+$H) 611.12 and 613.10.

Compound A-4: (7-(4-(4-(2,3-dichlorophenyl)piperazin-1-yl)butoxy)-2-oxo-3,4-dihydroquinolin-1(2H)-yl)methyl hexanoate

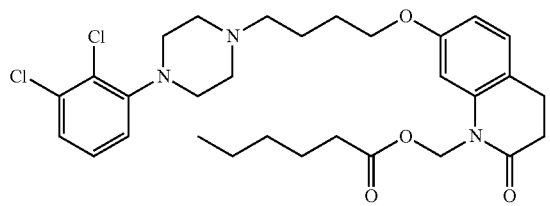 [SMILES: CCCCCC(=O)OCN1C(=O)CCc2ccc(OCCCCN3CCN(c4cccc(Cl)c4Cl)CC3)cc21]

Compound A-4 was prepared in an analogous fashion to Compound A-28. The desired product was isolated as a yellow solid (3.69 g, 87% yield). $^1$H NMR (CDCl$_3$, 300 MHz) δ 0.78 (t, 3H), 1.11-1.28 (m, 4H), 1.40-1.78 (m, 6H), 2.20-2.40 (m, 4H), 2.40-2.60 (m, 6H), 2.73-2.81 (m, 2H), 2.85-3.00 (m, 4H), 3.88-4.00 (m, 2H), 5.75-5.83 (m, 2H), 6.55-6.62 (m, 2H), 7.03-7.12 (m, 2H), 7.20-7.26 (m, 2H). m/z (M$^+$H) 576.4 and 578.4.

Olanzapine Prodrugs

Synthesis of chloromethyl 2-methyl-4-(4-methylpiperazin-1-yl)-5H-benzo[b]thieno[2,3-e][1,4]diazepine-5-carboxylate [A]

To a solution of olanzapine (18.0 g, 57.7 mmol) and triethylamine (16 mL, 0.12 mol) in dichloromethane (250 mL) was warmed to 35° C. and once a clear solution formed, the reaction was cooled to 5° C. To this was added chloromethyl chloroformate (7.6 mL, 86.5 mmol) over 20 minutes. The reaction was stirred at room temperature for 30 min and allowed to warm to room temperature. After 15 min at room temperature the reaction mixture was diluted with dichloromethane (100 mL), then washed with aq satd NaHCO$_3$ (75 mL) and water (350 mL). The organic phase was dried over MgSO$_4$ and filtered. The organic phase was then concentrated under vacuum at 45° C. to a volume of ~150 mL. The mixture was diluted with ethyl acetate (30 mL) and ~20-30 mL further was evaporated under vacuum. The mixture was cooled to room temperature and the resulting solid precipitate filtered and washed with ethyl acetate. After drying under vacuum at 35° C. for 90 min chloromethyl 2-methyl-4-(4-methylpiperazin-1-yl)-5H-benzo[b]thieno[2,3-e][1,4]diazepine-5-carboxylate [A] (17.1 g, 73%) was obtained as a yellow solid. $^1$H-NMR (300 MHz, CDCl$_3$) δ 7.62-7.14 (4H, m), 6.27-6.22 (1H, m), 5.84-5.69 (1H, m), 5.47-5.23 (1H, m), 3.89-3.63 (4H, m), 2.66-2.22 (10H, m).

General Procedure for the Synthesis of Aliphatic Carboxylic Acid Substituted Compounds Derived from [A1]:

To a solution of chloromethyl 2-methyl-4-(4-methylpiperazin-1-yl)-5H-benzo[b]thieno[2,3-e][1,4]diazepine-5-carboxylate [A](1 equiv) in dimethylformamide ((13 mL/g of [A])) was added cesium carbonate (1 equiv) and the appropriate aliphatic carboxylic acid (2 equiv). The reaction mixture was heated at 60° C. for 2-6 h, until starting material [A] had been consumed (loss of starting material determined by TLC). The reaction mixture was cooled, diluted with saturated aqueous NaHCO$_3$ (50 mL/g of [A]) and diethyl ether (75 mL/g of [A]). After being stirred for 15 min the mixture was filtered through celite and the organic phase separated. This was dried over MgSO$_4$ and evaporated. The residue was purified by column chromatography on silica eluting with 30% THF in EtOAc and the product containing fraction combined and evaporated. The residue was co-evaporated from hexanes.

Compound O-56: (palmitoyloxy)methyl 2-methyl-4-(4-methylpiperazin-1-yl)-5H-benzo[b]thieno[2,3-e][1,4]diazepine-5-carboxylate

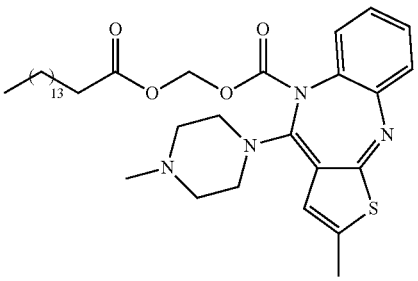

Using the procedure as described above with the exception of heating at 60° C. for 1 day gave (palmitoyloxy)methyl 2-methyl-4-(4-methylpiperazin-1-yl)-5H-benzo[b]thieno[2,3-e][1,4]diazepine-5-carboxylate (1.51 g, 75%) as a yellow oil. $^1$H NMR (300 MHz, CDCl$_3$) δ 7.62-7.55 (1H, m), 7.45-7.21 (2H, m), 7.17-7.08 (1H, m), 6.26-6.20 (1H, m), 5.66-5.35 (2H, m), 3.90-3.79 (2H, m), 3.68-3.54 (2H, m), 2.47-2.45 (4H, m), 2.33-2.24 (8H, m), 1.61-1.50 (2H, m), 1.35-1.15 (24H, m), 0.92-0.81 (3H, m)

Compound O-111: (stearoyloxy)methyl 2-methyl-4-(4-methylpiperazin-1-yl)-5H-benzo[b]thieno[2,3-e][1,4]diazepine-5-carboxylate

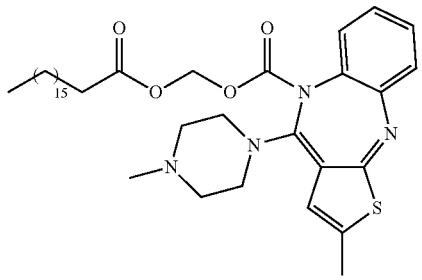

Using the procedure as described above gave (stearoyloxy)methyl 2-methyl-4-(4-methylpiperazin-1-yl)-5H-benzo[b]thieno[2,3-e][1,4]diazepine-5-carboxylate (1.51 g, 75%) as a yellow oil. $^1$H-NMR (300 MHz, CDCl$_3$) δ 7.63-7.54 (1H, m), 7.46-7.37 (1H, m), 7.36-7.26 (1H, m), 7.18-7.07 (1H, m), 6.28-6.19 (1H, m), 5.67-5.56 (1.5H, m), 5.38-5.34 (1H, m), 3.91-3.78 (2H, m), 3.69-3.54 (2H, m), 2.50-2.40 (4H, m), 2.31-2.24 (6H, m), 1.61-1.50 (2H, s), 1.34-1.20 (30H, m), 0.87 (3H, t). [M+H]$^+$=653.14.

Compound O-112: (icosanoyloxy)methyl 2-methyl-4-(4-methylpiperazin-1-yl)-5H-benzo[b]thieno[2,3-e][1,4]diazepine-5-carboxylate

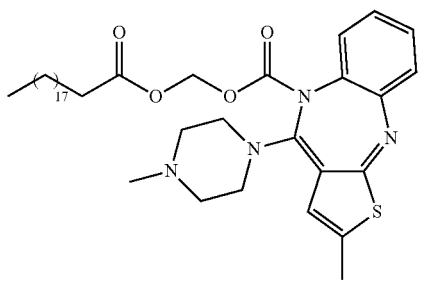

Using the procedure as described above gave (icosanoyloxy)methyl 2-methyl-4-(4-methylpiperazin-1-yl)-5H-benzo[b]thieno[2,3-e][1,4]diazepine-5-carboxylate (1.51 g, 75%) as a yellow oil. $^1$H-NMR (300 MHz, CDCl$_3$) δ 7.63-7.54 (1H, m), 7.46-7.37 (1H, m), 7.36-7.26 (1H, m), 7.18-7.07 (1H, m), 6.28-6.19 (1H, m), 5.67-5.57 (1.5H, m), 5.37-5.34 (1H, m), 3.90-3.78 (2H, m), 3.69-3.53 (2H, m), 2.49-2.40 (4H, m), 2.32-2.24 (6H, m), 1.61-1.50 (2H, s), 1.34-1.20 (34H, m), 0.87 (3H, t). [M+H]$^+$=681.19.

General Procedure for the Synthesis of Compounds 7-9

Synthesis of chloromethyl 2-methyl-4-(4-methylpiperazin-1-yl)-10H-benzo[b]thieno[2,3-e][1,4]diazepine-10-carboxylate [C]

To a solution of olanzapine (5.0 g, 16 mmol) in tetrahydrofuran (50 mL) at −78° C. was added tetramethylethylenediamine (2.4 mL, 16 mmol), followed by 2M n-BuLi in hexanes (8.0 mL, 16 mmol) over 5 min. The reaction mixture was stirred for 15 min and then chloromethyl chloroformate (2.1 mL, 24 mmol) added and the reaction mixture stirred a further 30 min. The reaction mixture was then warmed to room temperature, stirred for 1 h and quenched with water (50 mL). This mixture was diluted with brine (50 mL) and extracted with ethyl acetate (50 mL). The organic phase was dried over MgSO$_4$, evaporated and the residue further purified by column chromatography on silica eluting with 0.2:1:1 methanol/dichloromethane/ethyl acetate to give chloromethyl 2-methyl-4-(4-methylpiperazin-1-yl)-10H-benzo[b]thieno[2,3-e][1,4]diazepine-10-carboxylate [C] (5.6 g, ~50% pure by $^1$H NMR and LCMS). This was used directly in the next reaction without further purification. $^1$H-NMR (300 MHz, CDCl$_3$) δ 7.02-7.30 (4H, m), 6.45 (1H, s), 5.78-5.92 (1.5H, m), 5.52-5.60 (0.5H, m), 3.50-3.70 (4H, m), 2.35-2.55 (7H, m), 2.32 (3H, s). [M+H]$^+$=405.0

General Procedure for the Synthesis of Aliphatic Carboxylic Acid Substituted Compounds Derived from [C]:

To a solution of chloromethyl 2-methyl-4-(4-methylpiperazin-1-yl)-10H-benzo[b]thieno[2,3-e][1,4]diazepine-10-carboxylate (C:1 equiv) in dimethylformamide (13 mL/g of [C]) was added Cs$_2$CO$_3$ (1 equiv) and the appropriate aliphatic carboxylic acid (2 equiv). The reaction mixture was heated at 65° C. for 2-6 h, until starting material [A] had been consumed (loss of starting material determined by TLC). The reaction mixture was cooled, diluted with saturated aqueous NaHCO$_3$ (50 mL/g of [C]) and ethyl acetate (75 mL/g of [C]). After being stirred for 15 min the mixture was filtered through celite and the organic phase separated. This was dried over MgSO$_4$ and evaporated. The residue was further purified by column chromatography on silica eluting with 1:9 methanol/ethyl acetate and after evaporation of the product containing fractions, the residue was co-evaporated with hexane (2×10 mL/g [C]).

Compound O-7: (hexadecanoyloxy)methyl 2-methyl-4-(4-methylpiperazin-1-yl)-10H-benzo[b]thieno[2,3-e][1,4]diazepine-10-carboxylate

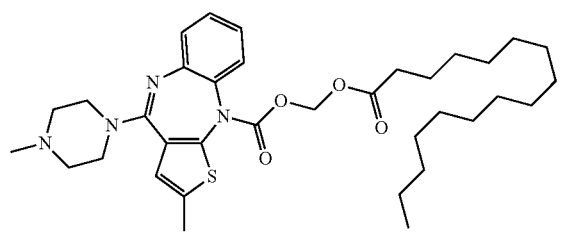 [SMILES: CCCCCCCCCCCCCCCC(=O)OCOC(=O)N1c2ccccc2N=C(N2CCN(C)CC2)c2cc(C)sc21]

Using the general procedure described above, employing palmitic acid and 1.0 g of the intermediate [C], provided (hexadecanoyloxy)methyl 2-methyl-4-(4-methylpiperazin-1-yl)-10H-benzo[b]thieno[2,3-e][1,4]diazepine-10-carboxylate (Compound O-7) (1.60 g, 39% yield) as a pale yellow oil. ¹H-NMR (300 MHz, CDCl₃) δ 7.00-7.25 (4H, m), 6.43 (1H, s), 5.62-5.90 (2H, m), 3.51-3.66 (4H, m), 2.30-2.56 (10H, m), 1.58-1.68 (2H, m), 1.20-1.34 (26H), 0.87 (3H, t). [M+H]⁺=625.07.

Compound O-8: (stearoyloxy)methyl 2-methyl-4-(4-methylpiperazin-1-yl)-10H-benzo[b]thieno[2,3-e][1,4]diazepine-10-carboxylate

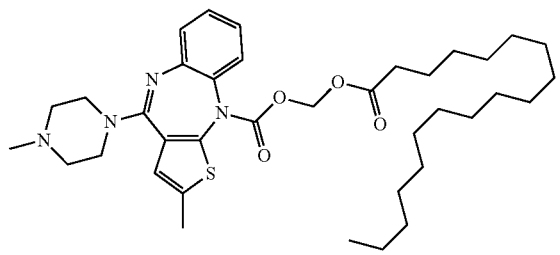 [SMILES: CCCCCCCCCCCCCCCCCC(=O)OCOC(=O)N1c2ccccc2N=C(N2CCN(C)CC2)c2cc(C)sc21]

Using the general procedure described above, employing stearic acid and 2.8 g of the intermediate [C], provided (stearoyloxy)methyl 2-methyl-4-(4-methylpiperazin-1-yl)-10H-benzo[b]thieno[2,3-e][1,4]diazepine-10-carboxylate (Compound O-8) (1.44 g, 32% yield) as a pale yellow oil. ¹H-NMR (300 MHz, CDCl₃) δ 6.99-7.22 (4H, m), 6.43 (1H, s), 5.62-5.88 (2H, m), 3.51-3.66 (4H, m), 2.30-2.66 (10H, m), 1.55-1.70 (2H, m), 1.20-1.34 (30H), 0.87 (3H, t). [M+H]⁺=653.21.

Compound O-9: (arachidoyloxy)methyl 2-methyl-4-(4-methylpiperazin-1-yl)-10H-benzo[b]thieno[2,3-e][1,4]diazepine-10-carboxylate

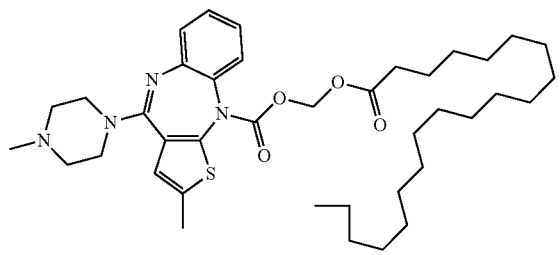 [SMILES: CCCCCCCCCCCCCCCCCCCC(=O)OCOC(=O)N1c2ccccc2N=C(N2CCN(C)CC2)c2cc(C)sc21]

Compound O-9 can be made using the general procedure described above, and by employing arachidic acid and the intermediate [C], which could then provide (arachidoyloxy)methyl 2-methyl-4-(4-methylpiperazin-1-yl)-10H-benzo[b]thieno[2,3-e][1,4]diazepine-10-carboxylate (Compound O-9).

The invention claimed is:

1. A pharmaceutical composition consisting of:
   (a) compound A-7:

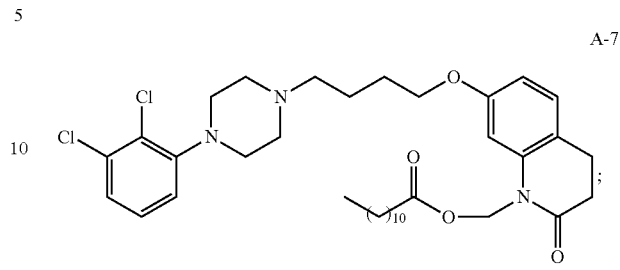

(b) a glycerol ester, wherein the glycerol ester is sesame oil;
   (c) an aqueous vehicle selected from the group consisting of sterile water, bacteriostatic water for injection, sterile saline solution, Ringer's solution, dextrose solution, phosphate buffer, citrate buffer, tartrate buffer, and acetate buffer; and
   (d) polysorbate 20;
   wherein the composition forms an aqueous, flocculated, injectable suspension.

2. The pharmaceutical composition of claim 1, wherein (a) and (b) are present at a ratio that results in flocs comprising component (a), wherein the flocs settle to a bed height that is greater than the sediment height of a formulation without component (b), such that components (a) and (b) can be resuspended for injection.

3. The pharmaceutical composition of claim 1, wherein (b) and (d) are present at a ratio that results in flocs of component (a) wherein the flocs settle to a bed height that is greater than the sediment height of a formulation without components (b) and (d), such that components (a), (b) and (d) can be resuspended for injection.

4. The pharmaceutical composition of claim 2, wherein (a) and (b), and optionally (d), can be resuspended for injection within 1-60 seconds of handshaking.

5. The pharmaceutical composition of claim 2, wherein the ratio of (a) to (b) and (a), (b) and (d) are such that the composition can be injected using a 20 or greater gauge needle.

6. The pharmaceutical composition of claim 1, wherein the ratio of (b) to (d) is approximately 0.5-1 to 20 to 1, by weight.

7. The pharmaceutical composition of claim 1, wherein the concentration of (a) is approximately 5-15 weight percent.

8. An injectable pharmaceutical composition consisting of:
   (a) approximately 5-35 weight percent compound A-7:

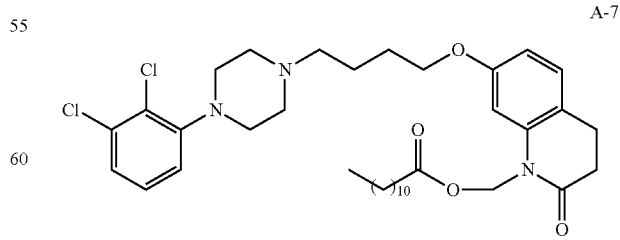

(b) approximately 0.3-20 weight percent of a glycerol ester, wherein the glycerol ester is sesame oil;
   (c) approximately 0-1 weight percent polysorbate 20 and (d) an aqueous carrier selected from the group consisting of sterile water, bacteriostatic water for injection, sterile saline solution, Ringer's solution, dextrose solution, phosphate buffer, citrate buffer, tartrate buffer, and acetate buffer.

9. A method for treating disorders of the central nervous system, comprising administering an effective amount of the composition of claim 1 to an individual in need of such treatment.

10. A pharmaceutical composition consisting of:
(a) 15-35 weight percent compound A-7:

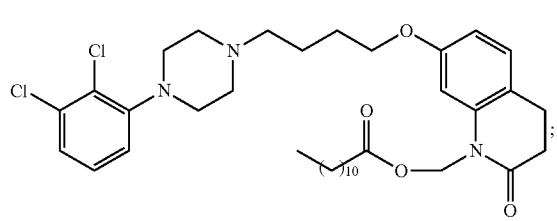

(b) 0.1-20 weight percent of a glycerol ester, wherein the glycerol ester is sesame oil;

(c) 0.05-1.0 weight percent polysorbate 20; and (d) an aqueous carrier selected from the group consisting of sterile water, bacteriostatic water for injection, sterile saline solution, Ringer's solution, dextrose solution, phosphate buffer, citrate buffer, tartrate buffer, and acetate buffer.

11. The composition of claim 1, wherein the sterile saline solution is phosphate-buffered saline.

12. The composition of claim 8, wherein the sterile saline solution is phosphate-buffered saline.

13. The composition of claim 10, wherein the sterile saline solution is phosphate-buffered saline.

\* \* \* \* \*